(12) United States Patent
Magnani et al.

(10) Patent No.: US 7,728,117 B2
(45) Date of Patent: Jun. 1, 2010

(54) HETEROBIFUNCTIONAL PAN-SELECTIN INHIBITORS

(75) Inventors: John L. Magnani, Gaithersburg, MD (US); John T. Patton, Jr., Gaithersburg, MD (US); Arun K. Sarkar, North Potomac, MD (US); Sergei A. Svarovsky, North Potomac, MD (US); Beat Ernst, Magden (CH)

(73) Assignee: GlycoMimetics, Inc., Gaithersburg, MD (US)

( * ) Notice: Subject to any disclaimer, the term of this patent is extended or adjusted under 35 U.S.C. 154(b) by 943 days.

(21) Appl. No.: 11/515,343

(22) Filed: Sep. 1, 2006

(65) Prior Publication Data

US 2007/0054870 A1    Mar. 8, 2007

Related U.S. Application Data

(60) Provisional application No. 60/713,994, filed on Sep. 2, 2005.

(51) Int. Cl.
*C07H 17/04* (2006.01)
*C07H 15/22* (2006.01)

(52) U.S. Cl. .................... 536/16.7; 536/16.6; 536/18.7; 536/123.1; 536/123.13

(58) Field of Classification Search ................ 536/16.6, 536/16, 7, 123.13, 123.1, 18.7
See application file for complete search history.

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | 530/387 |
| 4,859,769 A | 8/1989 | Karlsson et al. | 536/53 |
| 4,876,199 A | 10/1989 | Hakomori | 530/387 |
| 4,925,796 A | 5/1990 | Bergh et al. | 435/97 |
| 4,946,830 A | 8/1990 | Pulverer et al. | 514/23 |
| 5,143,712 A | 9/1992 | Brandley et al. | 424/1.1 |
| 5,151,360 A | 9/1992 | Handa et al. | 435/240.2 |
| 5,211,937 A | 5/1993 | Brandley et al. | 424/1.1 |
| 5,268,364 A | 12/1993 | Kojima et al. | 514/25 |
| 5,304,640 A | 4/1994 | Lasky et al. | 536/23.5 |
| 5,352,670 A | 10/1994 | Venot et al. | 514/54 |
| 5,369,096 A | 11/1994 | Yamada et al. | 514/61 |
| 5,412,123 A | 5/1995 | Rao et al. | 552/290 |
| 5,444,050 A | 8/1995 | Kogan et al. | 514/25 |
| 5,464,778 A | 11/1995 | Cummings et al. | 436/503 |
| 5,464,815 A | 11/1995 | Chamow et al. | 514/8 |
| 5,470,843 A | 11/1995 | Stahl et al. | 514/61 |
| 5,484,891 A | 1/1996 | Lasky et al. | 530/387.3 |
| 5,486,536 A | 1/1996 | Ward et al. | 514/460 |
| 5,519,008 A | 5/1996 | Rao et al. | 514/26 |
| 5,527,785 A | 6/1996 | Bevilacqua et al. | 514/56 |
| 5,538,724 A | 7/1996 | Butcher et al. | 424/152.1 |
| 5,559,103 A | 9/1996 | Gaeta et al. | 514/54 |
| 5,576,305 A | 11/1996 | Ratcliffe | 514/25 |
| 5,580,858 A | 12/1996 | Ippolito et al. | 514/25 |
| 5,580,862 A | 12/1996 | Rosen et al. | 514/61 |
| 5,589,465 A | 12/1996 | Ishida et al. | 514/25 |
| 5,604,207 A | 2/1997 | DeFrees et al. | 514/25 |
| 5,618,785 A | 4/1997 | Heavner et al. | 514/2 |
| 5,622,937 A | 4/1997 | Kogan et al. | 514/25 |
| 5,639,734 A | 6/1997 | Esko et al. | 514/25 |
| 5,646,123 A | 7/1997 | Ippolito et al. | 514/25 |
| 5,646,248 A | 7/1997 | Sawada et al. | 530/350 |
| 5,648,344 A | 7/1997 | Brandley et al. | 514/61 |
| 5,654,282 A | 8/1997 | Tang et al. | 514/25 |
| 5,654,412 A | 8/1997 | Srivastava et al. | 536/18.5 |
| 5,658,880 A | 8/1997 | Dasgupta et al. | 514/8 |
| 5,663,151 A | 9/1997 | Martel et al. | 514/25 |
| 5,679,321 A | 10/1997 | Dasgupta et al. | 424/9.1 |
| 5,679,644 A | 10/1997 | Rao et al. | 514/26 |
| 5,686,426 A | 11/1997 | Martel et al. | 514/25 |
| 5,693,621 A | 12/1997 | Toepfer et al. | 514/25 |
| 5,695,752 A | 12/1997 | Rosen et al. | 424/94.61 |
| 5,710,023 A | 1/1998 | Collins et al. | 435/69.1 |
| 5,710,123 A | 1/1998 | Heavner et al. | 514/2 |
| 5,723,583 A | 3/1998 | Seed et al. | 530/387.3 |
| 5,728,685 A | 3/1998 | Abbas et al. | 514/53 |
| 5,739,300 A | 4/1998 | Toepfer et al. | 536/4.1 |

(Continued)

FOREIGN PATENT DOCUMENTS

EP     319253 A2    6/1989

(Continued)

OTHER PUBLICATIONS

Abraham, W.M. et al., "Selectin Blockade Prevents Antigen-induced Late Bronchial Response and Airway Hyperresponsiveness in Allergic Sheep," *Am J. Respir Crit Care Med.* 159: 1205-1214, 1999.

(Continued)

*Primary Examiner*—Shaojia Anna Jiang
*Assistant Examiner*—Everett White
(74) *Attorney, Agent, or Firm*—Seed IP Law Group PLLC

(57) ABSTRACT

Compounds and methods are provided for modulating in vitro and in vivo processes mediated by selectin binding. More specifically, selectin modulators and their use are described, wherein the selectin modulators that modulate (e.g., inhibit or enhance) a selectin-mediated function comprise particular glycomimetics alone or linked to a member of a class of compounds termed BASAs (Benzyl Amino Sulfonic Acids) or a member of a class of compounds termed BACAs (Benzyl Amino Carboxylic Acids).

1 Claim, 23 Drawing Sheets

U.S. PATENT DOCUMENTS

| | | | |
|---|---|---|---|
| 5,747,463 A | 5/1998 | Marinier et al. | 514/25 |
| 5,750,508 A | 5/1998 | Dasgupta et al. | 514/25 |
| 5,753,617 A | 5/1998 | Heavner et al. | 514/9 |
| 5,753,631 A | 5/1998 | Paulson et al. | 514/25 |
| 5,763,413 A | 6/1998 | Numata et al. | 514/25 |
| 5,763,582 A | 6/1998 | Rao et al. | 536/53 |
| 5,789,385 A | 8/1998 | Anderson et al. | 514/25 |
| 5,789,573 A | 8/1998 | Baker et al. | 536/24.5 |
| 5,795,958 A | 8/1998 | Rao et al. | 530/331 |
| 5,811,404 A | 9/1998 | De Frees et al. | 514/25 |
| 5,811,405 A | 9/1998 | Toepfer et al. | 514/25 |
| 5,817,742 A | 10/1998 | Toepfer et al. | 528/328 |
| 5,827,817 A | 10/1998 | Larsen et al. | 514/2 |
| 5,827,837 A | 10/1998 | Bevilacqua et al. | 514/103 |
| 5,830,871 A | 11/1998 | Wong et al. | 514/23 |
| 5,837,689 A | 11/1998 | Anderson et al. | 514/25 |
| 5,837,690 A | 11/1998 | Rao et al. | 514/26 |
| 5,840,679 A | 11/1998 | Larsen et al. | 514/8 |
| 5,854,218 A | 12/1998 | DeFrees | 514/25 |
| 5,858,983 A | 1/1999 | Seed et al. | 514/23 |
| 5,858,994 A | 1/1999 | Kretzschmar et al. | 514/62 |
| 5,880,091 A | 3/1999 | Cummings et al. | 514/8 |
| 5,916,910 A | 6/1999 | Lai | 514/423 |
| 5,919,768 A | 7/1999 | Korgan et al. | 514/25 |
| 5,919,769 A | 7/1999 | Tsukida et al. | 514/25 |
| 5,962,422 A | 10/1999 | Nagy et al. | 514/25 |
| 5,976,540 A | 11/1999 | Rittershaus et al. | 424/184.1 |
| 5,977,080 A | 11/1999 | Rosen et al. | 514/25 |
| 5,985,852 A | 11/1999 | Nagy et al. | 514/54 |
| 5,994,402 A | 11/1999 | Rotstein et al. | 514/547 |
| 6,001,819 A | 12/1999 | Simon et al. | 514/54 |
| 6,001,988 A | 12/1999 | Parma et al. | 536/24.3 |
| 6,033,665 A | 3/2000 | Yednock et al. | 424/130.1 |
| 6,037,333 A | 3/2000 | Panjwani | 514/62 |
| 6,110,897 A | 8/2000 | Unverzagt et al. | 514/25 |
| 6,111,065 A | 8/2000 | Heavner et al. | 530/300 |
| 6,120,751 A | 9/2000 | Unger | 424/9.51 |
| 6,121,233 A | 9/2000 | Magnani et al. | 514/8 |
| 6,124,267 A | 9/2000 | McEver et al. | 514/25 |
| 6,133,239 A | 10/2000 | Handa et al. | 514/25 |
| 6,133,240 A | 10/2000 | Taylor et al. | 514/25 |
| 6,136,790 A | 10/2000 | Toepfer et al. | 514/25 |
| 6,169,077 B1 | 1/2001 | Oehrlein | 514/25 |
| 6,177,547 B1 | 1/2001 | Cummings et al. | 530/388.22 |
| 6,187,754 B1 | 2/2001 | Oehrlein | 514/25 |
| 6,193,973 B1 | 2/2001 | Tuttle | 424/195.1 |
| 6,193,979 B1 | 2/2001 | Rittershaus et al. | 424/195.11 |
| 6,197,752 B1 | 3/2001 | Schmidt et al. | 514/23 |
| 6,225,071 B1 | 5/2001 | Cummings et al. | 435/7.24 |
| 6,235,309 B1 | 5/2001 | Nagy et al. | 424/450 |
| 6,280,932 B1 | 8/2001 | Parma et al. | 435/6 |
| 6,309,639 B1 | 10/2001 | Cummings et al. | 424/143.1 |
| 6,387,884 B1 | 5/2002 | Magnani et al. | 514/25 |
| 6,391,857 B1 | 5/2002 | Magnani et al. | 514/25 |
| 6,407,135 B1 | 6/2002 | Lai et al. | 514/423 |
| 6,465,434 B1 | 10/2002 | Magnani et al. | 514/23 |
| 6,492,332 B1 | 12/2002 | Demopulos et al. | 514/12 |
| 6,503,885 B1 | 1/2003 | Kiso et al. | 514/25 |
| 6,528,487 B1 | 3/2003 | Heavner et al. | 514/13 |
| 2001/0046970 A1 | 11/2001 | Nagy et al. | 514/53 |
| 2001/0051370 A1 | 12/2001 | Bistrup et al. | 435/193 |
| 2002/0026033 A1 | 2/2002 | Cummings et al. | 530/322 |
| 2002/0028205 A1 | 3/2002 | Holgersson et al. | 424/184.1 |
| 2002/0031508 A1 | 3/2002 | Wagner et al. | 424/94.63 |
| 2002/0040008 A1 | 4/2002 | Wagner et al. | 514/41 |
| 2002/0132220 A1 | 9/2002 | Berens et al. | 435/1.1 |
| 2002/0164336 A1 | 11/2002 | Harrison et al. | 424/146.1 |
| 2002/0164748 A1 | 11/2002 | Bistrup et al. | 435/193 |
| 2002/0182366 A1 | 11/2002 | Stewart et al. | 424/146.1 |
| 2003/0012787 A1 | 1/2003 | Ashkenazi et al. | 424/145.1 |
| 2003/0012790 A1 | 1/2003 | Ashkenazi et al. | 424/178.1 |
| 2003/0018181 A1 | 1/2003 | Larsen et al. | 536/23.4 |
| 2003/0039683 A1 | 2/2003 | Cantrell et al. | 424/450 |

FOREIGN PATENT DOCUMENTS

| | | |
|---|---|---|
| EP | 381310 A1 | 8/1990 |
| EP | 408859 B2 | 8/1995 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 99/42130 | 8/1999 |
| WO | WO 99/43353 | 9/1999 |
| WO | WO 99/43356 | 9/1999 |
| WO | WO 02/22820 | 3/2002 |
| WO | WO 02/062810 | 8/2002 |
| WO | WO 03/097658 | 11/2003 |
| WO | WO 2004/004636 | 1/2004 |
| WO | WO 2004/058304 | 7/2004 |
| WO | WO 2006/127906 | 11/2006 |

OTHER PUBLICATIONS

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266(32):21537-21547, 1991.

Bänteli, R. et al., "Potent E-Selectin Antagonists," *Helvetica Chimica Acta* 83(11): 2893-2907, 2000.

Berg et al., "A Carbohydrate Domain Common to Both Sialyl Le$^a$ and Sialyl Le$^x$ Is Recognized by the Endothelial Cell Leukocyte Adhesion Molecule ELAM-1," *J. Biol. Chem.* 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," *J. Exp. Med.* 174:1461-1466, 1991.

Bird and Kimber, "Oligosaccharides Containing Fucose Linked α(1-3) and α(1-4) to *N*-Acetylglucosamine Cause Decompaction of Mouse Morulae," *Devel. Biol.* 104:449-460, 1984.

Bowen et al., "Characterization of a Human Homologue of the Murine Peripheral Lymph Node Homing Receptor," *Journal of Cell Biology* 109:421-427, 1989.

Brandley et al., "Carbohydrate Ligands of LEC Cell Adhesion Molecules," *Cell* 63:861-863, 1990.

Broquet et al., "Effect of Desipramine on a Glycoprotein Sialyltransferase Activity in C6 Cultured Glioma Cells," *J. Neurochem.* 54:388-394, 1990.

Childs et al., "High-molecular-weight glycoproteins are the major carriers of the carbohydrate differentiation antigens I, i and SSEA-1 of mouse teratocarcinoma cells," *Biochem. J.* 215:491-503, 1983.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, 1990.

Datta and Takayama, "Isolation and purification of trehalose 6-mono- and 6,6'-di-corynomycolates from *Cornyebacterium matruchotii*. Structural characterization of $^1$H NMR," *Carbohydrate Research* 245: 151-158, 1993.

Duijvestijn et al., "High Endothelial Differentiation in Human Lymphoid and Inflammatory Tissues Defined by Monoclonal Antibody HECA-452," *Am. J. Path.* 130:147-155, 1988.

Dupré, B. et al., "Glycomimetic Selectin Inhibitors: (α-D-Mannopyranosyloxy)methylbiphenyls," *Bioorganic & Medicinal Chemistry Letters* 6(5): 569-572, 1996.

Edgington, "How Sweet It Is: Selectin-Mediating Drugs," *Biotechnology* 10: 383-389, 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun.* 158(3):913-920, 1989.

Eggens et al., "Specific Interaction between $Le^x$ and $Le^x$ Determinants. A Possible Basis for Cell Recognition in Preimplantation Embryos and in Embryonal Carcinoma Cells," *J. Biol. Chem.* 264(16):9476-9484, 1989.

Ernst and Oehrlein, "Substrate and donor specificity of glycosyl transferases," *Glycoconjugate Journal* 16: 161-170, 1999.

Fenderson et al., "A Multivalent Lacto-N-Fucopenataose III-Lysyllysine Conjugate Decompacts Preimplantation Mouse Embryos, While the Free Oligosaccharide is Ineffective," *J. Exp. Med.* 160:1591-1596, 1984.

Fenderson et al., "Coordinate Expression of X and Y Haptens during Murine Embryogenesis," *Devel. Biol.* 114:12-21, 1986.

Fenderson et al., "The blood group I antigen defined by monoclonal antibody C6 is a marker of early mesoderm during murine embryogenesis," *Differentiation* 38:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," *J. Biol. Chem.* 259(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside ($VI^3NeuAcV^3III^3Fuc_2nLc_6$)," *J. Biol. Chem.* 259(16):10511-10517, 1984.

Gabius et al., "Endogenous Tumor Lectins: Overview and Perspectives," *Anticancer Res.* 6:573-578, 1986.

Gallatin et al., "A cell-surface molecule involved in organ-specific homing of lymphocyctes," *Nature* 304:30-34, 1983.

Gooi et al., "Stage-specific embryonic antigen involves α 1 → 3 fucosylated type 2 blood group chains," *Nature* 292:156-158, 1981.

Hakomori et al., "Novel Fucolipids Accumulating in Human Adenocarcinoma. I. Glycolipids With Di- or Trifucosylated Type 2 Chain," *J. Biol. Chem.* 259(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Comm.* 100(4):1578-1586, 1981.

Hakomori S., "Aberrant Glycosylation in Cancer Cell Membranes as Focused on Glycolipids: Overview and Perspectives," *Cancer Res.* 45:2405-2414, 1985.

Handa et al., "Selectin GMP-140 (CD62; PADGEM) Binds to Sialosyl-$Le^a$ and Sialosyl-$Le^x$, and Sulfated Glycans Modulate this Binding," *Biochemical and Biophysical Research Communication* 181(3):1223-1230, 1991.

Hansson and Zopf, "Biosynthesis of the Cancer-associated Sialyl-$Le^a$ Antigen," *Journal of Biological Chemistry* 260(16):9388-9392, 1985.

Hasegawa et al., "Synthesis of deoxy-L-fucose-containing sialyl Lewis X ganglioside analogues," *Carbohydrate Research* 257: 67-80, 1994.

Hasegawa et al., "Synthesis of sialyl Lewis X ganglioside analogues containing modified L-fucose residues," *Carbohydrate Research* 274: 165-181, 1995.

Holmes et al., "Enzymatic Basis for the Accumulation of Glycolipids with X and Dimeric X Determinants in Human Lung Cancer Cells (NCI-H69)," *J. Biol. Chem.* 260(12):7619-7627, 1985.

Huse et al., "Generation of a Large Combinatorial Library of the Immunoglobulin Repertoire in Phage Lambda," *Science* 246:1275-1281, 1989.

Hynes, R., "Integrins: A Family of Cell Surface Receptors," *Cell* 48:549-554, 1987.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology* 147:4178-4184, 1991.

Itai, S. et al., "Differentiation-dependent Expression of I and Sialyl I Antigens in the Developing Lung of Human Embryos and in Lung Cancers," *Cancer Research* 50: 7603-7611, 1990.

Jeffrey et al., "Affinity Chromatography of Carbohydrate-Specific Immunoglobulins: Coupling of Oligosaccharides to Sepharose," *Biochem. Biophys. Res. Commun.* 62:608-613, 1975.

Jentsch, K.D. et al., "Inhibition of Human Immunodeficiency Virus Type I Reverse Transcriptase by Suramin-related Compounds," *The Journal of General Virology* 68(8): 2183-2192, 1987.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," *J. Biol. Chem.* 258(14):8934-8942, 1983.

Kannagi et al., "Stage-specific embryonic antigens (SSEA-3 and -4) are epitopes of a unique globo-series ganglioside isolated from human teratocarcinoma cells," *Embo J.* 2(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys.* 11:311-315, 1990.

Kitagawa et al., "Characterization of Mucin-Type Oligosaccharides With the Sialyl-$Le^a$ Structure From Human Colorectal Adenocarcinoma Cells," *Biochem. Biophys. Res. Commun.* 178(3):1429-1436, 1991.

Kitagawa et al., "Immunoaffinity Isolation of a Sialyl-$Le^a$ Oligosaccharide from Human Milk," *J. Biochem.* 104:591-594, 1988.

Kogan, T.P. et al., "Rational Design and Synthesis of Oligosaccharide Mimetics: Selectin Antagonists as Cell Adhesion Inhibitors," *Abstracts of Papers, 210th ACS National Meeting*, American Chemical Society, Chicago, IL, Aug. 20-24, 1995, MEDI-18.

Köhler and Milstein, "Continuous cultures of fused cells secreting antibody of predefined specificity," *Nature* 256:495-497, 1975.

Köhler and Milstein, "Derivation of specific antibody-producing tissue culture and tumor lines by cell fusion," *Eur. J. Immunol.* 6:511-519, 1976.

Kojima and Hakomori, "Specific Interaction between Gangliotriaosylceramide ($G_{g3}$) and Sialosyllactosylceramide ($G_{M3}$) as a Basis for Specific Cellular Recognition between Lymphoma and Melanoma Cells," *J. Biol. Chem.* 264(34):20159-20162, 1989.

Koprowski et al., "Colorectal Carcinoma Antigens Detected by Hybridoma Antibodies," *Somatic Cell Genetics* 5(6):957-972, 1979.

Kogan, T.P. et al., "Novel Synthetic Inhibitors of Selectin-Mediated Cell Adhesion: Synthesis of 1,6-Bis[3-(3-carboxymethylphenyl)-r-(2-α-D-monnopyranosyloxy)phenyl]hexane (TBC1269)," *J Med. Chem* 41:1099-1111, 1998.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," *J. Med. Chem.* 38: 4976-4984, Dec. 22, 1995.

Kuzuoka, "Antitumor activity of murine monoclonal antibody NCC-ST-421," *Chem. Ab.* 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→°) Structural Element Revealed by 500-Mhz H NMR Spectroscopy," *Journal of Biological Chemistry* 259(14):9051-9058, 1984.

Larsen et al., PADGEM-Dependent Adhesion of Platelets to Monocytes and Neutrophils is Mediated by a Lineage-Specific Carbohydrate, LNF III (CD15), *Cell* 63:467-474, 1990.

Lindenberg et al., "Carbohydrate binding properties of mouse embryos," *J. Reprod. Fert.* 89:431-439, 1990.

Lipartiti et al., "Monosialoganglioside GM1 Reduces NMDA Neurotoxicity in Neonatal Rat Brain," *Experimental Neurology* 113:301-305, 1991.

Lowe et al., "A transfected human fucosyltransferase cDNA determines biosynthesis of oligosaccharide ligand(s) for endothelial-leukocyte adhesion molecule I," *Biochem. Soc. Trans.* 19(3):649-653, 1991.

Lowe et al., "ELAM-1-Dependent Cell Adhesion to Vascular Endothelium Determined by a Transfected Human Fucosyltransferase cDNA," *Cell* 63:475-484, 1990.

Macher et al., "A Novel Carbohydrate, Differentiation Antigen on Fucogangliosides of Human Myeloid Cells Recognized by Monoclonal Antibody VIM-2," *Journal of Biological Chemistry* 263(21):10186-10191, 1988.

Magnani et al., "Identification of the Gastrointestinal and Pancreatic Cancer-associated Antigen Detected by Monoclonal Antibody 19-9 in the Sera of Patients as a Mucin," *Cancer Res.* 43:5489-5492, 1983.

Magnani et al., "A Monoclonal Antibody-defined Antigen Associated with Gastrointestinal Cancer Is a Ganglioside Containing Sialylated Lacto-N-fucopentaose II," *Journal of Biological Chemistry* 257(23):14365-14369, 1982.

Magnani, J., "Carbohydrate Sequences Detected by Murine Monoclonal Antibodies," *Chemistry and Physics of Lipids* 42:65-74, 1986.

Magnani, J., "Potent Glycomimetic Inhibitors of the Adhesion Molecule, PA-IlL, for the Bacterial Pathogen, *Pseudomonas auroginosa*," *Glycobiology* 13(11): 854, Abstract No. 104, Oct. 2003.

Mulligan and Berg, "Selection for animal cells that express the *Escherichia coli* gene coding for xanthine-gunine phosphoribosyltransferase," *Proc. Natl. Acad. Sci. USA* 78:2072-2076, 1981.

Nicolaou et al., "Total Synthesis of the Tumor-Associated Le$^x$ Family of Glycosphingolipids," *J. Amer. Chem. Soc.* 112:3693-3695, 1990.

Nudelman et al., "Novel Fucolipids of Human Adenocarcinoma: Disialosyl Le$^a$ Antigen (III$^4$FucIII$^6$NeuAcIV$^3$NeuAcLc$_4$) of Human Colonic Adenocarcinoma and the Monoclonal Antibody (FH7) Defining This Structure," *J. Biol. Chem.* 261:5487-5495, 1986.

Orhlein, R., "Carbohydrates and Derivatives as Potential Drug Candidates with Emphasis on the Selectin and Linear-B Area," *Mini Reviews in Medicinal Chemistry* 1: 349-361, 2001.

Palcic et al., "Enzymic Synthesis of Oligosaccharides Terminating in the Tumor-Associated Sialyl-Lewis-a Determinant," *Carbohydr. Res.* 190:1-11, 1989.

Palcic et al., "Regulation of N-Acetylglucosaminyltransferase V Activity. Kinetic Comparisons of Parental, Rous Sarcoma Virus-Transformed BHK, and $_L$-Phytohemagglutinin-Resistant BHK Cells Using Synthetic Substrates and an Inhibitory Substrate Analog," *J. Biol. Chem.* 265:6759-6769, 1990.

Palcic et al., "A Bisubstrate Analog Inhibitor for α(1→2)-Fucosyltransferase," *J. Biol. Chem.* 264:17174-17181, 1989.

Palma-Vargas, J.M. et al., "Small-Molecule Selectin Inhibitor Protects Against Liver Inflammatory Response After Ischemia and Reperfusion," *J. Am. Coll. Surg.* 185: 365-372, 1997.

Phillips et al., "ELAM-1 Mediates Cell Adhesion by Recognition of a Carbohydrate Ligand, Sialyl-Le$^x$," *Science* 250:1130-1132, 1990.

Picker et al., "The Neutrophil Selectin LECAM-1 Presents Carbohydrate Ligands to the Vascular Selectins ELAM-1 and GMP-140," *Cell* 66:921-933, 1991.

Prokazova et al., "Sialylated lactosylceramides. Possible inducers of non-specific immunosuppression and atherosclerotic lesions," *European Journal of Biochemistry* 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol.* 88:127-137, 1981.

Rice and Bevilacqua, "An Inducible Endothelial Cell Surface Glycoprotein Mediates Melanoma Adhesion," *Science* 246:1303-1306, 1989.

Ruoslahti and Pierschbacher, "New Perspectives in Cell Adhesion: RGD and Integrins," *Science* 238:491-497, 1987.

Sakurai et al., "Selection of a Monoclonal Antibody Reactive with a High-Molecular-Weight Glycoprotein Circulating in the Body Fluid of Gastrointestinal Cancer Patients," *Cancer Research* 48:4053-4058, 1988.

Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, 1989.

Scharfman, A. et al., "*Pseudomonas aeruginosa* binds to neoglycoconjugates bearing mucin carbohydrate determinants and predominantly to sialyl-Lewis x conjugates," *Glycobiology* 9(8): 757-764, 1999.

Scharfman, A. et al., "Recognition of Lewis x Derivatives Present on Mucins by Flagellar Components of *Pseudomonas aeruginosa*," *Infection and Immunity* 69(9): 5243-5248, Sep. 2001.

Shitara et al., "Application of Anti-Sialyl Le$^a$ Monoclonal antibody, KM231, for Immunotherapy of Cancer," *Anticancer Res.* 11:2003-2014, 1991.

Siuzdak et al., "Examination of the Sialyl Lewis X—Calcium Complex by Electrospray Mass Spectrometry," *Bioorganic & Medicinal Chemistry Letters* 4(24): 2863-2866, 1994.

Sprengard, U. et al., "Synthesis and Biological Activity of Novel Sialyl-Lewis$^x$ Conjugates," *Bioorganic & Medicinal Chemistry Letters* 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," *J. Biol. Chem.* 263(23):11374-11381, 1988.

Stephens and Cockett, "The construction of highly efficient and versatile set of mammalian expression vectors," *Nucleic Acids Research.* 17:7110, 1989.

Streeter et al., "Immunohistologic and Functional Characterization of a Vascular Addressin Involved in Lymphocyte Homing into Peripheral Lymph Nodes," *Journal of Cell Biology* 107: 1853-1862, 1988.

Stroud et al., "Extended Type 1 Chain Glycosphingolipids: Dimeric Le$^a$ (III$^4$V$^4$Fuc$_2$Lc$_6$) as Human Tumor-associated Antigen," *J. Biol. Chem.* 266(13):8439-8446, 1991.

Svenson and Lindberg, "Coupling of Acid Labile *Salmonella* Specific Oligosaccharides to Macromolecular Carriers," *J. Immunol. Meth.* 25:323-335, 1979.

Takada et al., "Adhesion of Human Cancer Cells to Vascular Endothelium Mediated by a Carbohydrate Antigen, Sialyl Lewis A$^1$," *Biochem. Biophys. Res. Commun.* 179(2):713-719, 1991.

Takeichi, M., "Cadherins: a molecular family essential for selective cell-cell adhesion and animal morphogenesis," *Trends Genet.* 3(8):213-217, 1987.

Thoma, G. et al., "A readily Available, Highly Potent E-Selectin Antagonist," *Angew. Chem. Int. Ed.* 40(19): 3644-3647, 2001.

Thoma, G. et al., "Preorganization of the Bioactive Conformation of Sialyl Lewis$^x$ Analogues Correlates with Their Affinity to E-Selectin," *Angew. Chem. Int. Ed.* 40(10): 1941-1945, 2001.

Thoma, G. et al., "Synthesis and Biological Evaluation of a Sialyl Lewis X Mimic with Significantly Improved E-selectin Inhibition," *Bioorganic & Medicinal Chemistry Letters* 11: 923-925, 2001.

Tilton, R.G., "Endotoxin-Induced Leukocyte Accumulation in Aqueous Fluid of Rats is Decreased by a Small Molecule Selectin," *Investigative Opthalmology & Visual Science* 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA* 79:626-629, 1982.

Tyrrell et al., "Structural requirements for the carbohydrate ligand of E-selectin," *Proc. Natl. Acad. Sci. USA* 88:10372-10376, 1991.

Waldmann, H. et al., "Synthesis of 2-Acetamindo-2-Deoxyglucosylasparagine Glyco-Tripeptide and -Pentapeptides by Selective C- and N-Terminal Elongation of the Peptide Chain," *Carbohydrate Research* 196: 75-93, 1990.

Walz et al., "Recognition by ELAM-1 of the Sialyl-Le$^X$ Determinant on Myeloid and Tumor Cells," *Science* 250:1132-1135, 1990.

Ward and Mulligan, "Blocking of adhesion molecules in vivo as anti-inflammatory therapy," *Immunology 1*: 165-171, 1994.

Whisler and Yates, "Regulation of Lymphocyte Responses by Human Gangliosides. I. Characteristics of Inhibitory Effects and the Induction of Impaired Activation," *Journal of Immunology* 125(5):2106-2111, 1980.

Yamazaki, F. et al., "Syntheisis of an appropriately protected core glycotetraoside, a key intermediate for the synthesis of 'bisected' complex-type glycans of a glycoprotein," *Carbohydrate Research* 201: 15-30, 1990.

Zhou et al., "The Selectin GMP-140 Binds to Sialylated, Fucosylated Lactosaminoglycans on Both Myeloid and Nonmyeloid Cells," *Journal of Cell Biology* 115(2):557-564, 1991.

Zopf et al., "Affinity Purification of Antibodies Using Oligosaccharide-Phenethylamine Derivatives Coupled to Sepharose," *Meth. Enzymol.* 50:171-175, 1978.

Acord, J. et al., "A rapid microplate method for quantifying inhibition of bacterial adhesion to eukaryotic cells," *Journal of Microbiological Methods* 60: 55-62, 2005.

Perret, S. et al., "Structural basis for the interaction between human milk oligosaccharides and the bacterial lectin PA-IIL of *Pseudomonas aeruginosa*," *Biochem. J.* 389: 325-332, 2005.

HETEROBIFUNCTIONAL PAN-SELECTIN INHIBITORS

CROSS-REFERENCE TO RELATED APPLICATION

This application claims the benefit under 35 U.S.C. §119(e) of U.S. Provisional Patent Application No. 60/713,994 filed Sep. 2, 2005, which application is incorporated herein by reference in its entirety.

BACKGROUND OF THE INVENTION

1. Field of the Invention

The present invention relates generally to compounds, compositions and methods for modulating processes mediated by selectin binding, and more particularly to selectin modulators and their use, wherein the selectin modulators that modulate a selectin-mediated function comprise particular glycomimetics alone or linked to a member of a class of compounds termed BASAs (Benzyl Amino Sulfonic Acids) or a member of a class of compounds termed BACAs (Benzyl Amino Carboxylic Acids).

2. Description of the Related Art

When a tissue is infected or damaged, the inflammatory process directs leukocytes and other immune system components to the site of infection or injury. Within this process, leukocytes play an important role in the engulfment and digestion of microorganisms. Thus, the recruitment of leukocytes to infected or damaged tissue is critical for mounting an effective immune defense.

Selectins are a group of structurally similar cell surface receptors that are important for mediating leukocyte binding to endothelial cells. These proteins are type 1 membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin and L-selectin. E-selectin is found on the surface of activated endothelial cells, which line the interior wall of capillaries. E-selectin binds to the carbohydrate sialyl-Lewis$^x$ (SLe$^x$), which is presented as a glycoprotein or glycolipid on the surface of certain leukocytes (monocytes and neutrophils) and helps these cells adhere to capillary walls in areas where surrounding tissue is infected or damaged; and E-selectin also binds to sialyl-Lewis$^a$ (SLe$^a$), which is expressed on many tumor cells. P-selectin is expressed on inflamed endothelium and platelets, and also recognizes SLe$^x$ and SLe$^a$, but also contains a second site that interacts with sulfated tyrosine. The expression of E-selectin and P-selectin is generally increased when the tissue adjacent to a capillary is infected or damaged. L-selectin is expressed on leukocytes. Selectin-mediated intercellular adhesion is an example of a selectin-mediated function.

Modulators of selectin-mediated function include the PSGL-1 protein (and smaller peptide fragments), fucoidan, glycyrrhizin (and derivatives), anti-selectin antibodies, sulfated lactose derivatives, and heparin. All have shown to be unsuitable for drug development due to insufficient activity, toxicity, lack of specificity, poor ADME characteristics and/or availability of material.

Although selectin-mediated cell adhesion is required for fighting infection and destroying foreign material, there are situations in which such cell adhesion is undesirable or excessive, resulting in tissue damage instead of repair. For example, many pathologies (such as autoimmune and inflammatory diseases, shock and reperfusion injuries) involve abnormal adhesion of white blood cells. Such abnormal cell adhesion may also play a role in transplant and graft rejection. In addition, some circulating cancer cells appear to take advantage of the inflammatory mechanism to bind to activated endothelium. In such circumstances, modulation of selectin-mediated intercellular adhesion may be desirable.

Accordingly, there is a need in the art for identifying inhibitors of selectin-mediated function, e.g., of selectin-dependent cell adhesion, and for the development of methods employing such compounds to inhibit conditions associated with excessive selectin activity. The present invention fulfills these needs and further provides other related advantages.

BRIEF SUMMARY OF THE INVENTION

Briefly stated, this invention provides compounds, compositions and methods for modulating selectin-mediated processes. In the present invention, the compounds that modulate (e.g., inhibit or enhance) a selectin-mediated function comprise a particular glycomimetic alone or linked to a BASA or a BACA. Such compounds may be combined with a pharmaceutically acceptable carrier or diluent to form a pharmaceutical composition. The compounds or compositions may be used in a method to modulate (e.g., inhibit or enhance) a selectin-mediated function, such as inhibiting a selectin-mediated intercellular adhesion.

In one aspect of the present invention, compounds are provided having the formula:

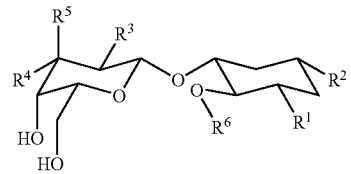

wherein:

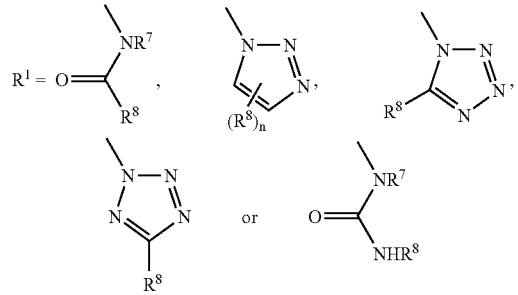

where n=0-2, and R$^8$ are independently selected where n=2;

R$^2$=H, —C(=O)OX where X is C$_1$-C$_8$ alkanyl, C$_1$-C$_8$ alkenyl, C$_1$-C$_8$ alkynyl or C$_1$-C$_{14}$ aryl, —C(=O)NH(CH$_2$)$_n$NH$_2$, —[C(=O)NH(CH$_2$)$_n$NHC(=O)]$_m$(L)$_m$Z, where n=0-30, m=0-1, L is a linker, and Z is a benzyl amino sulfonic acid, a benzyl amino carboxylic acid, a polyethylene glycol, or a second compound or salt thereof having the above formula to form a dimer where R$^2$ of the second compound or salt thereof has m=0, no Z, and is the point of attachment;

R³= —OH, 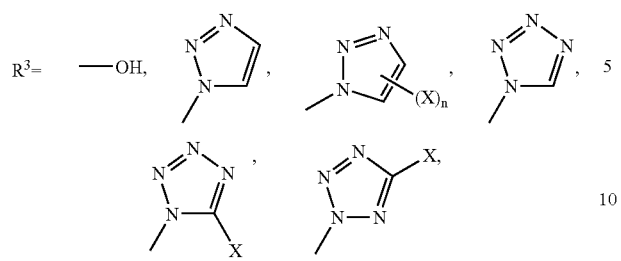

—O—C(=O)—X, —NH₂, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

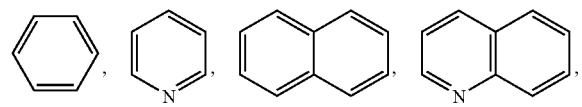

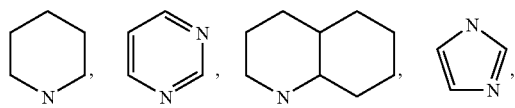

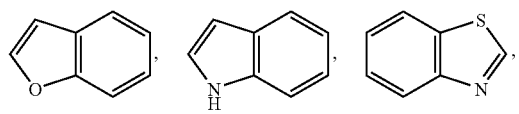

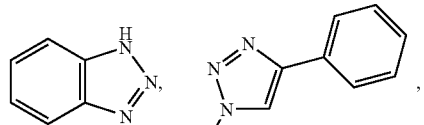

, and

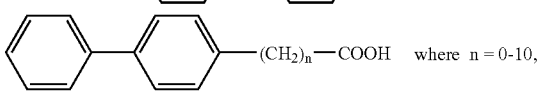  (CH₂)ₙ—COOH  where n = 0-10, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl, or OY where Y is H, $C_1$-$C_8$ alkanyl, $C_1$-$C_8$ alkenyl, $C_1$-$C_8$ alkynyl, or $C_1$-$C_{14}$ aryl;

R⁴ = 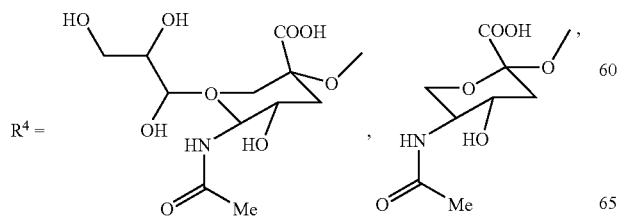

6'sulfated GlcNAc, 6'carboxylated GlcNAc, 6'sulfated GalNAc, 6'sulfated galactose, 6'carboxylated galactose or

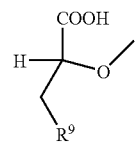

where $R^9$ is aryl, heteroaryl, cyclohexane, t-butane, adamantane, or triazole, and any of $R^9$ may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl;

$R^5$=H, or $R^4$ and $R^5$ are taken together to form

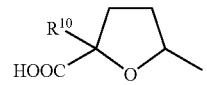

where $R^{10}$ is aryl, heteroaryl,

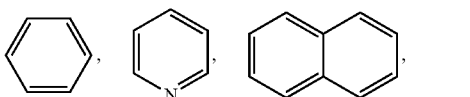

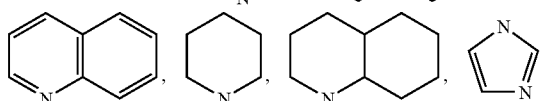

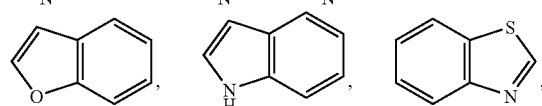

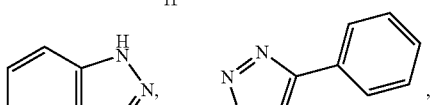, or

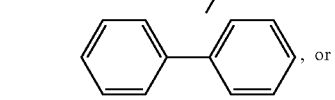  (CH₂)ₙ—COOH where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl;

$R^6$=H, fucose, mannose, arabinose, galactose or polyols;

$R^7$=H, $C_1$-$C_8$ alkanyl, $C_1$-$C_8$ alkenyl, $C_1$-$C_8$ alkynyl or

and $R^8$=H $C_1$-$C_8$ alkanyl, $C_1$-$C_8$ alkenyl, $C_1$-$C_8$ alkynyl,

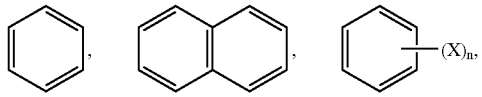

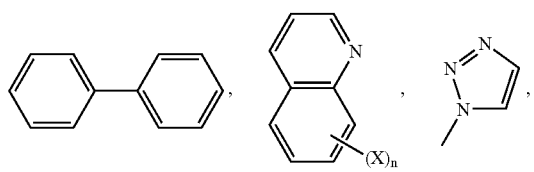

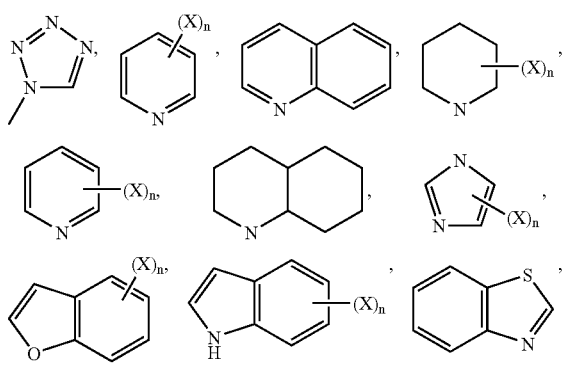

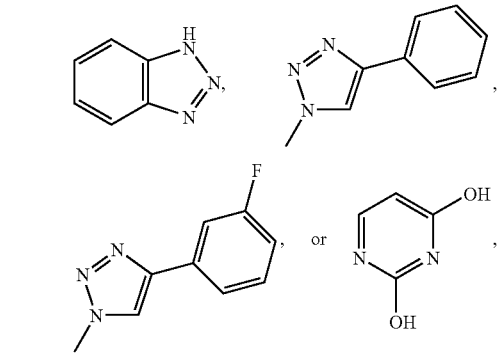

where n=0-3 and X is independently selected from H, OH, Cl, F, $N_3$, $NH_2$, $C_1$-$C_8$ alkanyl, $C_1$-$C_8$ alkenyl, $C_1$-$C_8$ alkynyl, $C_1$-$C_{14}$ aryl, $OC_1$-$C_8$ alkanyl, $OC_1$-$C_8$ alkenyl, $OC_1$-$C_8$ alkynyl, and $OC_1$-$C_{14}$ aryl, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl or OY where Y is H, $C_1$-$C_8$ alkanyl, $C_1$-$C_8$ alkenyl, $C_1$-$C_8$ alkynyl, or $C_1$-$C_{14}$ aryl.

A compound of the present invention includes physiologically acceptable salts thereof. A compound of the present invention in combination with a pharmaceutically acceptable carrier or diluent provides a composition of the present invention. In the chemical formulae herein, a line extending from an atom depicted or a carbon implied by the intersection of the two other lines, represents the point of attachment (and does not represent a methyl group).

In an embodiment of the present invention, $R^6$ is fucose:

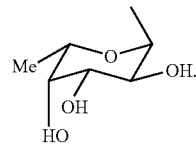

In an embodiment, $R^7$ is H.
In an embodiment, $R^4$ is

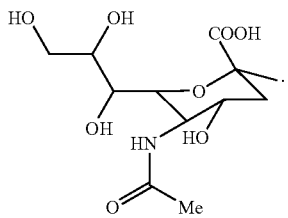

In an embodiment, $R^4$ is

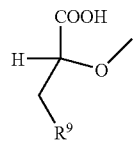

where $R^9$ is defined as for the general formula above.
In an embodiment, $R^9$ is cyclohexane.
In an embodiment, $R^6$ is galactose.
In an embodiment, $R^8$ is

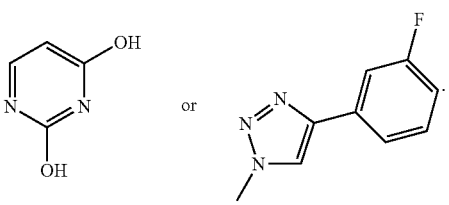

In an embodiment, $R^2$ is —[C(═O)NH($CH_2$)$_n$NHC(═O)]$_m$ (L)$_m$Z, where n, m, L and Z are defined as for the general formula above.
In an embodiment, Z is a benzyl amino sulfonic acid, a benzyl amino carboxylic acid or a polyethylene glycol.
In an embodiment, $R^3$ is —O—C(═O)—X, where X is defined as for the general formula above.
In an embodiment, X is

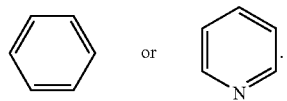

In an embodiment, $R^5$ is H.

In an embodiment, L is a polyethylene glycol or a thiadiazole.

In an embodiment, a compound comprises a compound according to the present invention, further comprising a diagnostic or therapeutic agent. Such a compound may be combined with a pharmaceutically acceptable carrier or diluent to form one embodiment of a composition of the present invention.

In another aspect of the present invention, methods are provided for using a compound or composition of the present invention to modulate a selectin-mediated function. Such a compound or composition can be used, for example, to inhibit or enhance a selectin-mediated function, such as selectin-mediated intercellular interactions. A compound or composition can be used in a method to contact a cell expressing a selectin in an amount effective to modulate the selectin's function. A compound or composition can be used in a method to administer to a patient, who is in need of having inhibited the development of a condition associated with an excessive selectin-mediated function (such as an excessive selectin-mediated intercellular adhesion), in an amount effective to inhibit the development of such a condition. Examples of such conditions include inflammatory diseases, autoimmune diseases, infection, cancer, shock, thrombosis, wounds, burns, reperfusion injury, platelet-mediated diseases, leukocyte-mediated lung injury, spinal cord damage, digestive tract mucous membrane disorders, osteoporosis, arthritis, asthma and allergic reactions. A compound or composition can be used in a method to administer to a patient who is the recipient of a transplanted tissue in an amount effective to inhibit rejection of the transplanted tissue. A compound or composition can be used in a method in an amount effective to target an agent (e.g., a diagnostic or therapeutic agent) to a selectin-expressing cell by contacting such a cell with the agent linked to the compound or composition. A compound or composition can be used in the manufacture of a medicament, for example for any of the uses recited above.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1A:
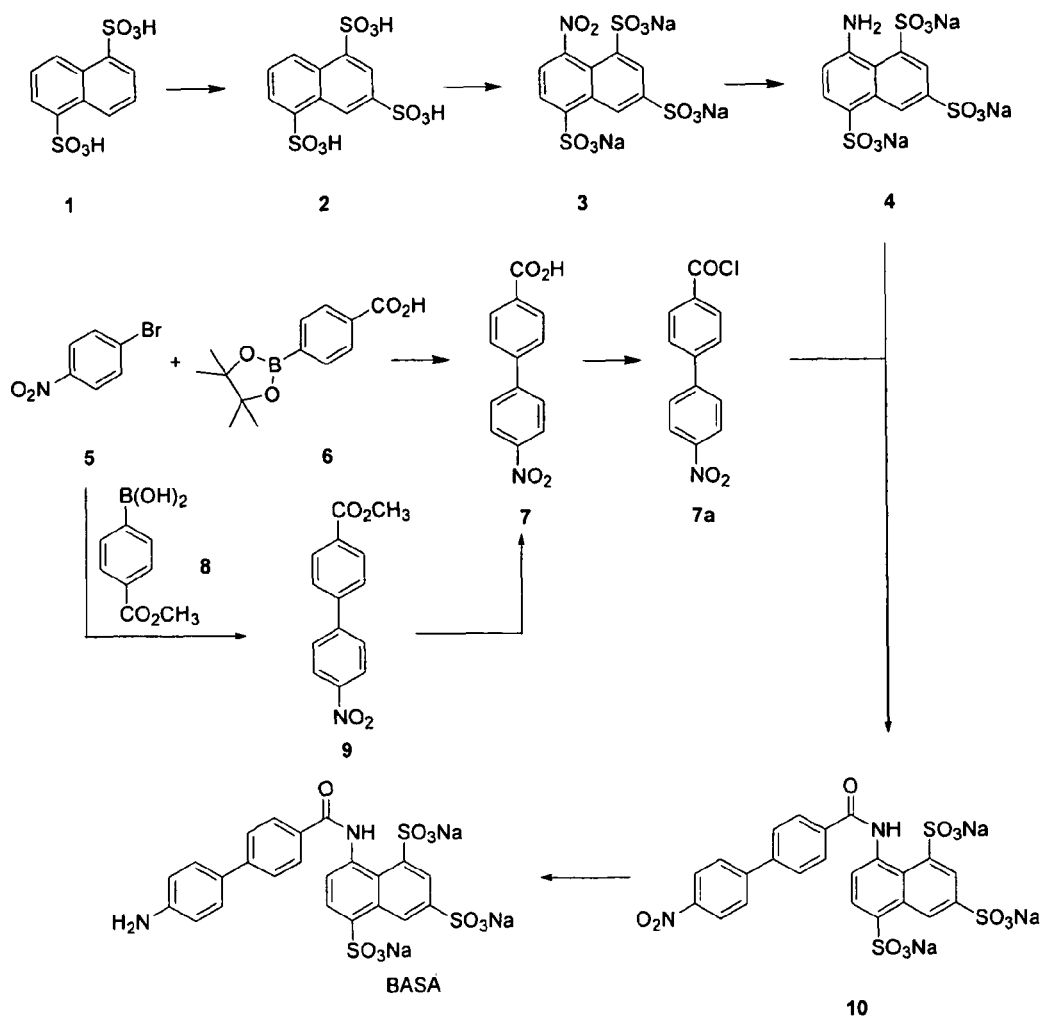
FIGS. 1A and 1B are diagrams illustrating the syntheses of BASAs.

As noted above, the present invention provides selectin modulators, compositions thereof and methods for modulating selectin-mediated functions. Such modulators may be used in vitro or in vivo, to modulate (e.g., inhibit or enhance) selectin-mediated functions in a variety of contexts, discussed in further detail below. Examples of selectin-mediated functions include intercellular adhesion and the formation of new capillaries during angiogenesis.

Selectin Modulators

The term "selectin modulator," as used herein, refers to a molecule(s) that modulates (e.g., inhibits or enhances) a selectin-mediated function, such as selectin-mediated intercellular interactions. A selectin modulator may consist entirely of a glycomimetic compound of the present invention, or may consist of such a glycomimetic linked to a BASA (Benzyl Amino Sulfonic Acid) or a BACA (Benzyl Amino Carboxylic Acid), or may comprise one or more additional molecular components to any of the above.

A selectin modulator of the present invention which does not possess a BASA or a BACA is preferably used to inhibit an E-selectin-mediated function. With the addition of a BASA or BACA to a glycomimetic of the present invention, the selectin modulator has increased ability to modulate P- and L-selectin-mediated functions as well.

A selectin modulator of the present invention is a compound or physiologically acceptable salt thereof, having the formula:

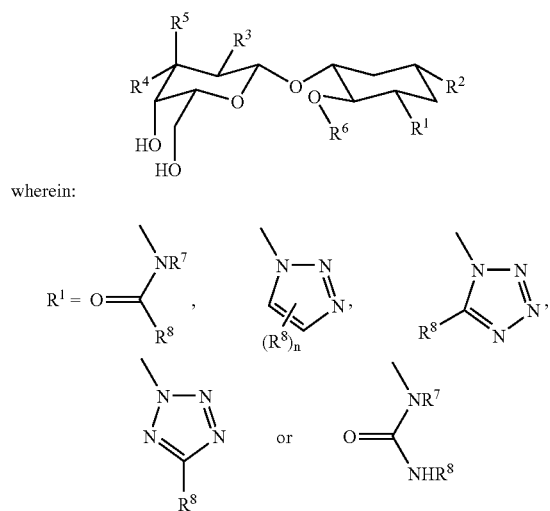

wherein:

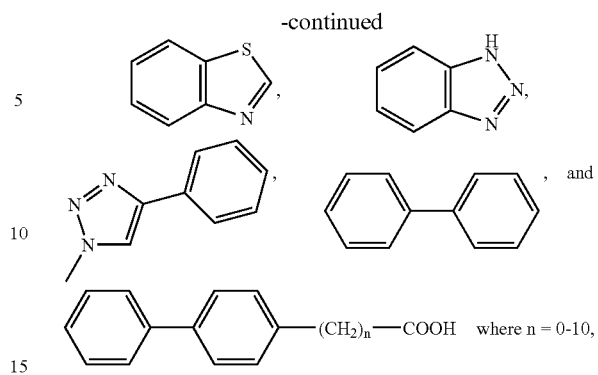

and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl, or OY where Y is H, $C_1$-$C_8$ alkanyl, $C_1$-$C_8$ alkenyl, $C_1$-$C_8$ alkynyl, or $C_1$-$C_{14}$ aryl;

where n=0-2, and $R^8$ are independently selected where n=2;

$R^2$=H, —C(=O)OX where X is $C_1$-$C_8$ alkanyl, $C_1$-$C_8$ alkenyl, $C_1$-$C_8$ alkynyl or $C_1$-$C_{14}$ aryl, —C(=O)NH(CH$_2$)$_n$NH$_2$,
—[C(=O)NH(CH$_2$)$_n$NHC(=O)]$_m$(L)$_m$Z, where n=0-30, m=0-1, L is a linker, and Z is a benzyl amino sulfonic acid, a benzyl amino carboxylic acid, a polyethylene glycol, or a second compound or salt thereof having the above formula to form a dimer where $R^2$ of the second compound or salt thereof has m=0, no Z, and is the point of attachment;

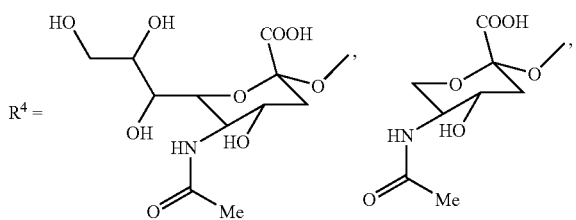

6'sulfated GlcNAc, 6'carboxylated GlcNAc, 6'sulfated GalNAc, 6'sulfated galactose, 6'carboxylated galactose or

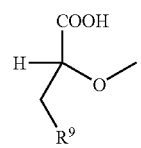

where $R^9$ is aryl, heteroaryl, cyclohexane, t-butane, adamantane, or triazole, and any of $R^9$ may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl;

$R^5$=H, or $R^4$ and $R^5$ are taken together to form

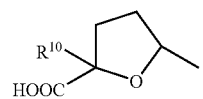

where $R^{10}$ is aryl, heteroaryl,

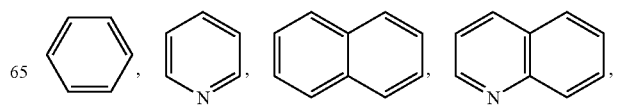

$R^3$= 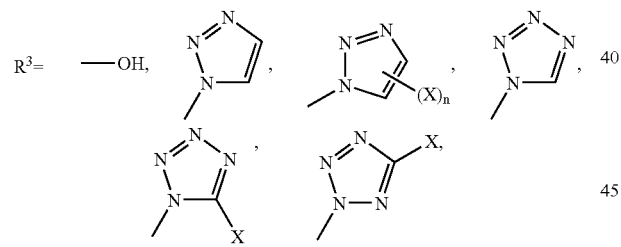

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

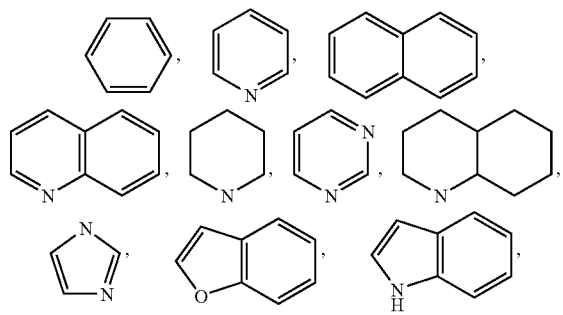

-continued

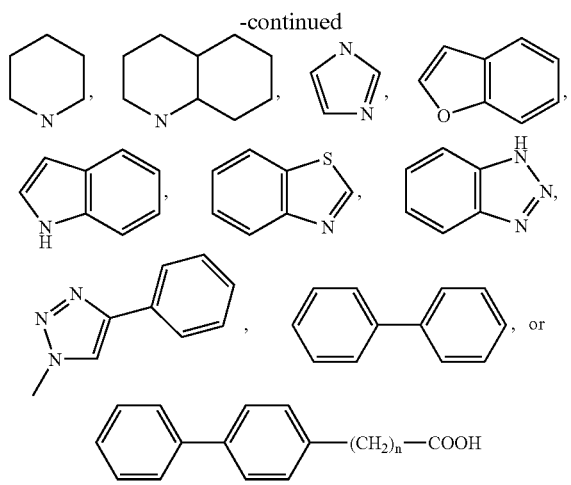

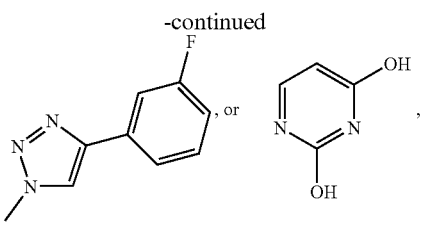

where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl;

$R^6$=H, fucose, mannose, arabinose, galactose or polyols;
$R^7$=H, $C_1$-$C_8$ alkanyl, $C_1$-$C_8$ alkenyl, $C_1$-$C_8$ alkynyl or

$R^8$=H, $C_1$-$C_8$ alkanyl, $C_1$-$C_8$ alkenyl, $C_1$-$C_8$ alkynyl,

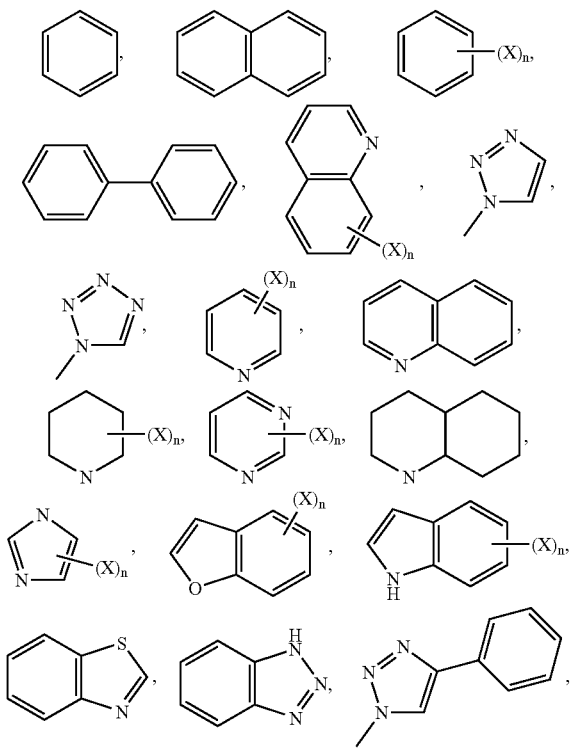

where n=0-3 and X is independently selected from H, OH, Cl, F, $N_3$, $NH_2$, $C_1$-$C_8$ alkanyl, $C_1$-$C_8$ alkenyl, $C_1$-$C_8$ alkynyl, $C_1$-$C_{14}$ aryl, $OC_1$-$C_8$ alkanyl, $OC_1$-$C_8$ alkenyl, $OC_1$-$C_8$ alkynyl, and $OC_1$-$C_{14}$ aryl, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl or OY where Y is H, $C_1$-$C_8$ alkanyl, $C_1$-$C_8$ alkenyl, $C_1$-$C_8$ alkynyl, or $C_1$-$C_{14}$ aryl.

As used herein, a "$C_1$-$C_8$ alkanyl" refers to an alkane substituent with one to eight carbon atoms and may be straight chain or branched. Examples are methyl, ethyl, propyl, isopropyl, butyl and t-butyl. A "$C_1$-$C_8$ alkenyl" refers to an alkene substituent with one to eight carbon atoms, at least one carbon-carbon double bond, and may be straight chain or branched. Examples are similar to "$C_1$-$C_8$ alkanyl" examples except possessing at least one carbon-carbon double bond. A "$C_1$-$C_8$ alkynyl" refers to an alkyne substituent with one to eight carbon atoms, at least one carbon-carbon triple bond, and may be straight chain or branched. Examples are similar to "$C_1$-$C_8$ alkanyl" examples except possessing at least one carbon-carbon triple bond. An "aryl" refers to an aromatic substituent with one to fourteen carbon atoms in one or multiple rings which may be separated by a bond or fused. A "heteroaryl" is similar to an "aryl" except the aromatic substituent possesses at least one heteroatom (such as N, O or S) in place of a ring carbon. Examples of aryls and heteroaryls include phenyl, naphthyl, pyridinyl, pyrimidinyl, triazolo, furanyl, oxazolyl, thiophenyl, quinolinyl and diphenyl. As used herein, the term "independently selected" refers to the selection of identical or different substituents.

As used herein, polyethylene glycol ("PEG") refers to multiple units of ethylene glycol, as well as those with one or more substituents (e.g., dicarboxylated PEG). PEGs with and without substituents are well known to those in the art. Within the present invention, PEG can serve as a substituent on a selectin modulator, or as a linker to attach other groups or compounds to a selectin modulator, or a selectin modulator may possess more than one PEG.

Where a second selectin modulator is linked to a first selectin modulator, a dimer of selectin modulators (i.e., a divalent molecule) is formed. A variety of linkers may be used to join the two selectin modulators. For example, PEG may be used as the linker to prepare a dimer. As used herein, a "dimer" can be a homodimer or a heterodimer. A homodimer refers to a dimer where the two selectin modulators joined together are identical (independent of the substituents for the linking to one another). A heterodimer refers to a dimer where the two selectin modulators (independent of the linkage substituents) are not identical.

A selectin modulator of the present invention may possess, at $R^4$ of the above formula, sialic acid or a sialic acid mimic as set forth above. For example, the hexose ring of sialic acid may be replaced with cyclohexane. The presence of sialic acid in the selectin modulator enhanced P-selectin binding.

Where only E-selectin binding (and not both E- and P-selecting binding) is desired, a sialic acid mimic replaces sialic acid in the selectin modulator.

Alternative to (or in combination with) the replacement of a sialic acid mimic with sialic acid, P-selectin binding may be enhanced by the addition of a BASA or a BACA. As disclosed above, the selectin modulator compounds of the present invention may possess a "Z" at $R^2$, and Z may be a BASA or a BACA. The addition of a BASA or BACA to a selectin modulator compound of the present invention that lacks sialic acid, can convert the selectin modulator from a compound that is selective for binding to E-selectin to one that binds both E- and P-selectin. BASA or BACA includes a portion or an analogue of a BASA or BACA or portion of either, provided that the compound retains the ability to modulate a selectin-mediated function. PEG may be added to a selectin modulator with or without a BASA (or BACA). PEG may also be used to link a BASA or BACA to a selectin modulator.

Within the present invention, BASAs are low molecular weight sulfated compounds which have the ability to interact with a selectin. The interaction modulates or assists in the modulation (e.g., inhibition or enhancement) of a selectin-mediated function (e.g., an intercellular interaction). They exist as either their protonated acid form, or as a sodium salt, although sodium may be replaced with potassium or any other pharmaceutically acceptable counterion. A representative BASA has the following structure:

Portions of BASA that retain the ability to interact with a selectin (which interaction modulates or assists in the modulation of a selectin-mediated function as described herein) are also a BASA component of the selectin modulators of the present invention. Such portions generally comprise at least one aromatic ring present within the BASA structure. Within certain embodiments, a portion may comprise a single aromatic ring, multiple such rings or half of a symmetrical BASA molecule.

As noted above, analogues of BASA and portions thereof (both of which possess the biological characteristic set forth above) are also encompassed, e.g., by the BASA component of the selectin modulators, within the present invention. As used herein, an "analogue" is a compound that differs from BASA or a portion thereof because of one or more additions, deletions and/or substitutions of chemical moieties, such that the ability of the analogue to inhibit a selectin-mediated interaction is not diminished. For example, an analogue may contain S to P substitutions (e.g., a sulfate group replaced with a phosphate group). Other possible modifications include: (a) modifications to ring size (e.g., any ring may contain between 4 and 7 carbon atoms); (b) variations in the number of fused rings (e.g., a single ring may be replaced with a polycyclic moiety containing up to three fused rings, a polycyclic moiety may be replaced with a single unfused ring or the number of fused rings within a polycyclic moiety may be altered); (c) ring substitutions in which hydrogen atoms or other moieties covalently bonded to a carbon atom within an aromatic ring may be replaced with any of a variety of moieties, such as F, Cl, Br, I, OH, O-alkyl (C1-8), SH, $NO_2$, CN, $NH_2$, NH-alkyl (C1-8), N-(alkyl)$_2$, $SO_3M$ (where $M=H^+$, $Na^+$, $K^+$ or other pharmaceutically acceptable counterion), $CO_2M$, $PO_4M_2$, $SO_2NH_2$, alkyl (C1-8), aryl (C6-10), $CO_2$-alkyl (C1-8), —$CF_2X$ (where X can be H, F, alkyl, aryl or acyl groups) and carbohydrates; and (d) modifications to linking moieties (i.e., moieties located between rings in the BASA molecule) in which groups such as alkyl, ester, amide, anhydride and carbamate groups may be substituted for one another.

Certain BASA portions and analogues contain one of the following generic structures:

Within this structure, n may be 0 or 1, $X^1$ may be —$PO_2M$, —$SO_2M$ or —$CF_2$— (where M is a pharmaceutically acceptable counterion such as hydrogen, sodium or potassium), $R^1$ may be —OH, —F or —$CO_2R^4$ (where $R^4$ may be —H or —$(CH_2)_m$—$CH_3$ and m is a number ranging from 0 to 3, $R^2$ may be —H, —$PO_3M_2$, —$SO_3M_2$, —$CH_2$—$PO_3M_2$, —$CH_2$—$SO_3M_2$, —$CF_3$ or —$(CH_2)_m$—$C(R^6)H$—$R^5$ or $R^9$—$N(R^{10})$—, $R^3$ may be —H, —$(CH_2)_m$—$C(R^6)H$—$R^5$ or $R^9$—$N(R^{10})$— (where $R^5$ and $R^6$ may be independently selected from —H, —$CO_2$—$R^7$ and —NH—$R^8$, $R^7$ and $R^8$ may be independently selected from hydrogen and moieties comprising one or more of an alkyl group, an aromatic moiety, an amino group or a carboxy group, and $R^9$ and $R^{10}$ may be independently selected from —H, —$(CH_2)_m$—$CH_3$; —$CH_2$—Ar, —CO—Ar, where m is a number ranging from 0 to 3 and Ar is an aromatic moiety (i.e., any moiety that comprises at least one substituted or unsubstituted aromatic ring, wherein the ring is directly bonded to the —$CH_2$— or —CO— group indicated above)).

Other portions and analogues of BASA comprise the generic structure:

Within this structure, $R_1$ and $R_2$ may be independently selected from (i) hydrogen, (ii) moieties comprising one or more of an alkyl group, an aromatic moiety, an amino group or a carboxy group, and (iii) —CO—$R_3$ (where $R_3$ comprises an alkyl or aromatic moiety as described above) and M is a pharmaceutically acceptable counterion.

The individual compounds, or groups of compounds, derived from the various combinations of the structures and substituents described herein, are disclosed by the present application to the same extent as if each compound or group of compounds was set forth individually. Thus, selection of particular structures and/or particular substituents is within the scope of the present invention.

Figure 1B:
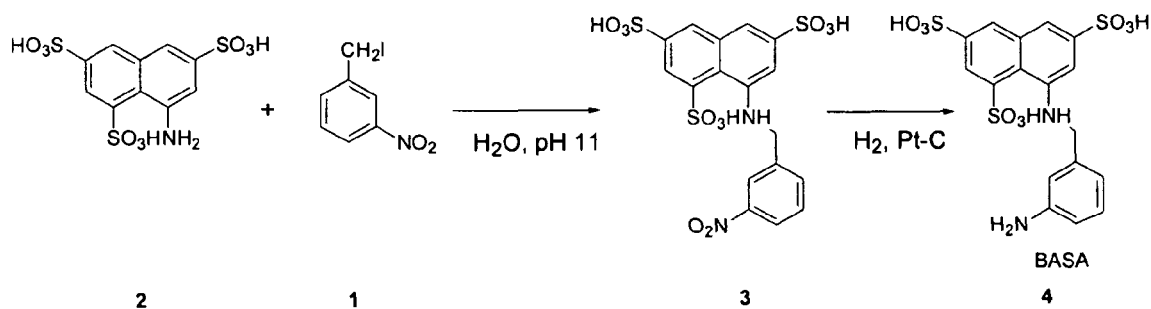

Representative BASA portions and analogues are included in the compounds shown in FIGS. 1A-1B. It will be apparent to those of ordinary skill in the art that modifications may be made to the compounds shown within these figures, without adversely affecting the ability to function as selectin modulators. Such modifications include deletions, additions and substitutions as described above.

A BACA is similar to a BASA, except instead of sulfonic acid groups, the compound possesses carboxylic acid groups. For example, the sulfonic acid groups of the above BASA compounds may be replaced with carboxylic acid groups. Thus, the above disclosure to BASAs is incorporated by reference into this description of BACAs.

Examples of BACAs include:

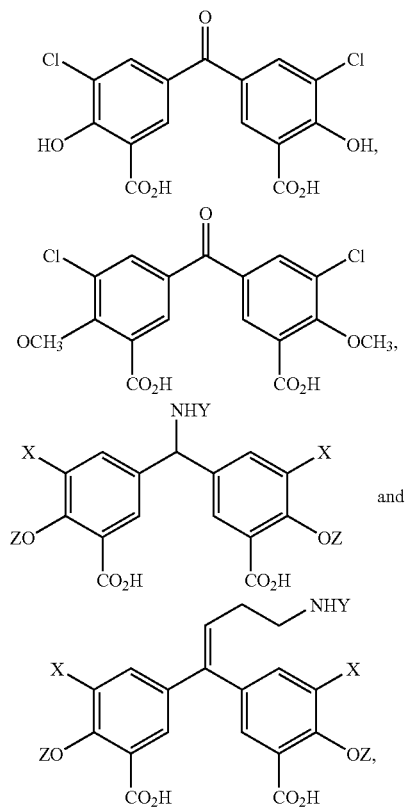

where X is F or Cl; Y is H, —C(=O)(O—CH$_2$CH$_2$)$_n$ or —C(=O)(CH$_2$)$_n$ wherein n=0-8; and Z is H, C$_1$-C$_8$ alkanyl, C$_1$-C$_8$ alkenyl or C$_1$-C$_8$ alkynyl.

As described above, a BASA or BACA may be joined to a compound of the present invention at R$^2$ via a linker ("L"). Typically a linker is first attached to one of a glycomimetic or a BASA/BACA, which is then reacted with the other. The attachment of a BASA or BACA to a particular glycomimetic can be accomplished in a variety of ways to form a selectin modulator. A linker possessed by (or added to) a BASA or BACA or a glycomimetic may include a spacer group, such as —(CH$_2$)$_n$— or —O(CH$_2$)$_n$— where n is generally about 1-20 (including any whole integer range therein). An example of a linker is —NH$_2$ on a glycomimetic, e.g., —CH$_2$—NH$_2$ when it includes a short spacer group. In an embodiment, —CH$_2$—NH$_2$ is attached to a glycomimetic at R' which may then be used to attach a BASA or BACA. The simplest attachment method is reductive amination of the BASA or BACA to a glycomimetic containing a reducing end (an anomeric hydroxyl/aldehyde). This is accomplished by simple reaction of the BASA or BACA to the reducing end and subsequent reduction (e.g., with NaCNBH$_3$ at pH 4.0) of the imine formed. The most general approach entails the simple attachment of an activated linker to the glycomimetic via an O, S or N heteroatom (or C atom) at the anomeric position. The methodology of such attachments has been extensively researched for carbohydrates and anomeric selectivity is easily accomplished by proper selection of methodology and/or protecting groups. Examples of potential glycosidic synthetic methods include Lewis acid catalyzed bond formation with halogen or peracetylated sugars (Koenigs Knorr), trichloroacetamidate bond formation, thioglycoside activation and coupling, glucal activation and coupling, n-pentenyl coupling, phosphonate ester homologation (Horner-Wadsworth-Emmons reaction), and many others. Alternatively, linkers could be attached to positions on the moieties other than the anomeric. The most accessible site for attachment is at a six hydroxyl (6-OH) position of a glycomimetic (a primary alcohol). The attachment of a linker at the 6-OH can be easily achieved by a variety of means. Examples include reaction of the oxy-anion (alcohol anion formed by deprotonation with base) with an appropriate electrophile such as an alkyl/acyl bromide, chloride or sulfonate ester, activation of the alcohol via reaction with a sulfonate ester chloride or POCl$_3$ and displacement with a subsequent nucleophile, oxidation of the alcohol to the aldehyde or carboxylic acid for coupling, or even use of the Mitsunobu reaction to introduce differing functionalities. Once attached the linker is then functionalized for reaction with a suitable nucleophile on the BASA or BACA (or vice versa). This is often accomplished by use of thiophosgene and amines to make thiourea-linked heterobifunctional ligands, diethyl squarate attachment (again with amines) and/or simple alkyl/acylation reactions. Additional methods that could be utilized include FMOC solid or solution phase synthetic techniques traditionally used for carbohydrate and peptide coupling and chemo-enzymatic synthesis techniques possibly utilizing glycosyl/fucosyl transferases and/or oligosaccharyltransferase (OST).

Embodiments of linkers include the following:

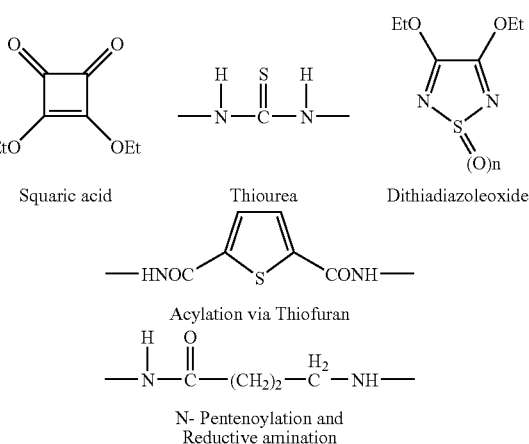

-continued

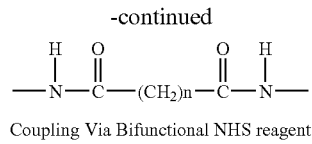

Coupling Via Bifunctional NHS reagent

Other linkers (e.g., PEG) will be familiar to those in the art or in possession of the present disclosure.

A compound, or physiologically acceptable salt thereof, of the present invention has the formula:

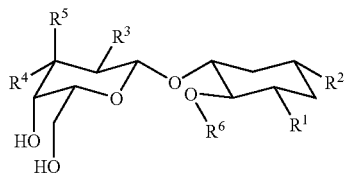

wherein $R^1$-$R^9$ are defined as set forth above.

In a preferred embodiment, $R^6$ is fucose:

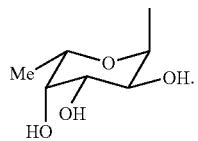

In a preferred embodiment, $R^7$ is H. In a preferred embodiment, $R^4$ is

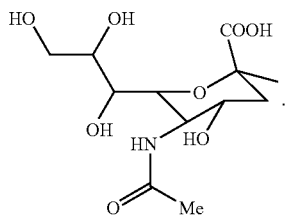

In a preferred embodiment, $R^4$ is

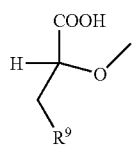

where $R^9$ is defined as above. In a preferred embodiment, $R^9$ is cyclohexane. In a preferred embodiment, $R^6$ is galactose. In a preferred embodiment, $R^8$ is

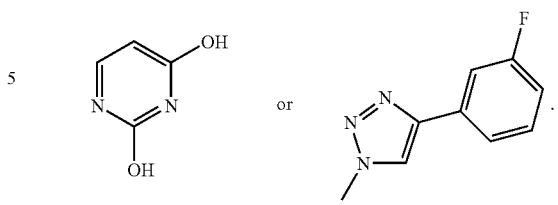

In a preferred embodiment, $R^2$ is
—[C(=O)NH(CH$_2$)$_n$NHC(=O)]$_m$(L)$_m$Z, where n, m, L and Z are defined as above. In a preferred embodiment, Z is a benzyl amino sulfonic acid, a benzyl amino carboxylic acid or a polyethylene glycol. In a preferred embodiment, $R^3$ is —O—C(=O)—X, where X is defined as above. In a preferred embodiment, X is

or

In a preferred embodiment, $R^5$ is H. In a preferred embodiment, L is a polyethylene glycol or a thiadiazole.

Although selectin modulators as described herein may sufficiently target a desired site in vivo, it may be beneficial for certain applications to include an additional targeting moiety to facilitate targeting to one or more specific tissues. As used herein, a "targeting moiety," may be any substance (such as a compound or cell) that, when linked to a modulating agent enhances the transport of the modulator to a target tissue, thereby increasing the local concentration of the modulator. Targeting moieties include antibodies or fragments thereof, receptors, ligands and other molecules that bind to cells of, or in the vicinity of, the target tissue. Linkage is generally covalent and may be achieved by, for example, direct condensation or other reactions, or by way of bi- or multi-functional linkers.

For certain embodiments, it may be beneficial to also, or alternatively, link a drug to a selectin modulator. As used herein, the term "drug" refers to any bioactive agent intended for administration to a mammal to prevent or treat a disease or other undesirable condition. Drugs include hormones, growth factors, proteins, peptides and other compounds. Examples of potential drugs include antineoplastic agents (such as 5-fluorouracil and distamycin), integrin agonist/antagonists (such as cyclic-RGD peptide), cytokine agonist/antagonists, histamine agonist/antagonists (such as diphenhydramine and chlorpheniramine), antibiotics (such as aminoglycosides and cephalosporins) and redox active biological agents (such as glutathione and thioredoxin). In other embodiments, diagnostic or therapeutic radionuclides may be linked to a selectin modulator. In many embodiments, the agent may be linked directly or indirectly to a selectin modulator.

Modulators as described herein may be present within a pharmaceutical composition. A pharmaceutical composition comprises one or more modulators in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more active agents, such as drugs (e.g., those set forth above), which may be linked to a modulator or may be free within the composition.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Selectin modulators are generally present within a pharmaceutical composition in a therapeutically effective amount. A therapeutically effective amount is an amount that results in a discernible patient benefit, such as increased healing of a condition associated with excess selectin-mediated function (e.g., intercellular adhesion), as described below.

In general, the modulating agents and compositions described herein may be used for enhancing or inhibiting a selectin-mediated function. Such enhancement or inhibition may be achieved in vitro and/or in vivo in a warm-blooded animal, preferably in a mammal such as a human, provided that a selectin-expressing cell is ultimately contacted with a modulator, in an amount and for a time sufficient to enhance or inhibit selectin-mediated function.

Within certain aspects, the present invention provides methods for inhibiting the development of a condition associated with a selectin-mediated function, such as intercellular adhesion. In general, such methods may be used to prevent, delay or treat such a condition. In other words, therapeutic methods provided herein may be used to treat a disease, or may be used to prevent or delay the onset of such a disease in a patient who is free of disease or who is afflicted with a disease that is not associated with a selectin-mediated function. For example, the therapeutic methods have uses that may include the arrest of cell growth, the killing of cells, the prevention of cells or cell growth, the delay of the onset of cells or cell growth, or the prolongation of survival of an organism.

A variety of conditions are associated with a selectin-mediated function. Such conditions include, for example, tissue transplant rejection, platelet-mediated diseases (e.g., atherosclerosis and clotting), hyperactive coronary circulation, acute leukocyte-mediated lung injury (e.g., adult respiratory distress syndrome (ARDS)), Crohn's disease, inflammatory diseases (e.g., inflammatory bowel disease), autoimmune diseases (MS, myasthenia gravis), infection, cancer (and metastasis), thrombosis, wounds (and wound-associated sepsis), burns, spinal cord damage, digestive tract mucous membrane disorders (gastritis, ulcers), osteoporosis, rheumatoid arthritis, osteoarthritis, asthma, allergy, psoriasis, septic shock, traumatic shock, stroke, nephritis, atopic dermatitis, frostbite injury, adult dyspnoea syndrome, ulcerative colitis, systemic lupus erythematosus, diabetes and reperfusion injury following ischaemic episodes. Selectin modulators may also be administered to a patient prior to heart surgery to enhance recovery. Other uses include pain management, prevention of restinosis associated with vascular stenting, and for undesirable angiogenesis, e.g., associated with cancer.

Selectin modulators of the present invention may be administered in a manner appropriate to the disease to be treated (or prevented). Appropriate dosages and a suitable duration and frequency of administration may be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a selectin modulator may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Selectin modulators may also be used to target substances to cells that express a selectin. Such substances include therapeutic agents and diagnostic agents. Therapeutic agents may be a molecule, virus, viral component, cell, cell component or any other substance that can be demonstrated to modify the properties of a target cell so as to provide a benefit for treating or preventing a disorder or regulating the physiology of a patient. A therapeutic agent may also be a prodrug that generates an agent having a biological activity in vivo. Molecules that may be therapeutic agents may be, for example, polypeptides, amino acids, nucleic acids, polynucleotides, steroids, polysaccharides or inorganic compounds. Such molecules may function in any of a variety of ways, including as enzymes, enzyme inhibitors, hormones, receptors, antisense oligonucleotides, catalytic polynucleotides, anti-viral agents, anti-tumor agents, anti-bacterial agents, immunomodulating agents and cytotoxic agents (e.g., radionuclides such as iodine, bromine, lead, palladium or copper). Diagnostic agents include imaging agents such as metals and radioactive agents (e.g., gallium, technetium, indium, strontium, iodine, barium, bromine and phosphorus-containing compounds), contrast agents, dyes (e.g., fluorescent dyes and chromophores) and enzymes that catalyze a colorimetric or fluorometric reaction. In general, therapeutic and diagnostic agents may be attached to a selectin modulator using a variety of techniques such as those described above. For targeting purposes, a selectin modulator may be administered to a patient as described herein. Since selectins are expressed on endothelial cells involved in the formation of new capillaries during angiogenesis, a selectin modulator may be used to target a therapeutic agent for killing a tumor's vasculature. A selectin modulator may also be used for gene targeting.

Selectin modulators may also be used in vitro, e.g., within a variety of well known cell culture and cell separation methods. For example, modulators may be linked to the interior surface of a tissue culture plate or other cell culture support, for use in immobilizing selectin-expressing cells for screens, assays and growth in culture. Such linkage may be performed by any suitable technique, such as the methods described above, as well as other standard techniques. Modulators may also be used, for example, to facilitate cell identification and sorting in vitro, permitting the selection of cells expressing a selectin (or different selectin levels). Preferably, the modulator(s) for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulator linked to a fluorescent marker, such as fluorescein, is contacted with the cells, which are then analyzed by fluorescence activated cell sorting (FACS).

Modulating agents as described above are capable, for example, of inhibiting selectin-mediated cell adhesion. This ability may generally be evaluated using any of a variety of in vitro assays designed to measure the effect on adhesion between selectin-expressing cells (e.g., adhesion between leukocytes or tumor cells and platelets or endothelial cells). For example, such cells may be plated under standard conditions that, in the absence of modulator, permit cell adhesion. In general, a modulator is an inhibitor of selectin-mediated cell adhesion if contact of the test cells with the modulator results in a discernible inhibition of cell adhesion. For example, in the presence of modulators (e.g., micromolar levels), disruption of adhesion between leukocytes or tumor cells and platelets or endothelial cells may be determined visually within approximately several minutes, by observing the reduction of cells interacting with one another.

All compounds of the present invention or useful thereto, include physiologically acceptable salts thereof.

The following Examples are offered by way of illustration and not by way of limitation.

EXAMPLES

Example 1

Synthesis of BASA (FIG. 1A)

Synthesis of compound 4: Nitration of commercially available 2 (1 g) is according to the procedure described (for literature conditions see U.S. Pat. No. 4,534,905; Allison, F. et al. *Helv. Chim. Acta* 4:2139 (1952)).

The crude product 3 is dissolved in water (40 mL) and 10% Pd/C (0.3 g) added. The mixture is hydrogenated (~45 psi) at room temperature for 48 h. The catalyst is filtered through Celite and the filter bed is washed with water. The filtrate is concentrated under vacuum to afford a pink solid. After removal of the catalyst, the filtrate is concentrated to 15 mL and an equal volume of ethanol is added. The precipitate is collected by filtration to give compound 4 with very little impurity.

Synthesis of compound 7a: A solution of 5 (5 g) and 8 (4.45 g, 24.7 mmol), and $K_2CO_3$ (2 M in $H_2O$, 24.7 mL, 49.4 mmol) in 10:1 toluene/ethanol (70 mL) is treated with $Pd(PPh_3)_4$ (1.43 g, 1.24 mmol) and the mixture is refluxed for 20 h. After work up, recrystallization of the crude product in EtOH and chromatographic purification of the recrystallization filtrate affords compound 9 (2.9 g, 46%, >90% HPLC) and 2.2 g of recovered 5. The product is characterized by $^1$H NMR.

A mixture of 9 (2.9 g, 11.3 mmol) and $LiOH.H_2O$ (1.43 g, 34.1 mmol) in 1:1 $THF/H_2O$ (250 mL) is stirred at RT for 21 h. The reaction affords 7 (2.58 g, 94%, >90% HPLC) after work up. The product is characterized by $^1$H NMR.

DMF (20 µl) is added to a suspension of 7 (500 mg, 1.94 mmol), $SOCl_2$ (0.23 mL, 3.10 mmol) and toluene (3 mL) and then heated to 80° C. After 20 h the reaction is worked up to afford the acid chloride (640 mg). The product 7a is characterized by IR and $^1$H NMR.

Synthesis of compound 10: To a solution of amine 4 (268 mg, 0.641 mmol) in $H_2O$ (2 mL) and dioxane (18 mL) is added a solution of 7a (273 mg, 0.99 mmol) in dioxane (16 mL) dropwise over 30 min. The pH of the reaction mixture is adjusted to 8.5 with 0.25 M NaOH as the addition progresses. The reaction is stirred at room temperature for 2.5 h after the addition. Purification by column chromatography (methanol/toluene 1:1) followed by prep. TLC (methanol/toluene 1:1) affords 50 mg of compound 10, which is characterized by $^1$H NMR and MS.

Hydrogenation of compound 10: A suspension of 10 (30 mg, 0.049 mmol) and 10% Pd on carbon (50 mg) in $H_2O$ (20 mL) is hydrogenated (55 psi) at room temperature for 4 h to yield the BASA of FIG. 1A.

Example 2

Synthesis of BASA (FIG. 1B)

Synthesis of compound 4: 3-nitro-benzyl iodide (1) (48.3 g) is added to an aqueous solution (pH 11) of commercially available, 8-aminonaphthalene-1,3,5-trisulfonic acid (2) (29.5 g) with stirring at room temperature. pH of the solution is adjusted to 1 and after evaporation of the solvent, the product 3 (6.4 g) is precipitated out from ethanol.

Platinum catalyzed hydrogenation of compound 3 affords compound 4 (the BASA of FIG. 1B) in 96% yield.

Example 3

Figure 2:
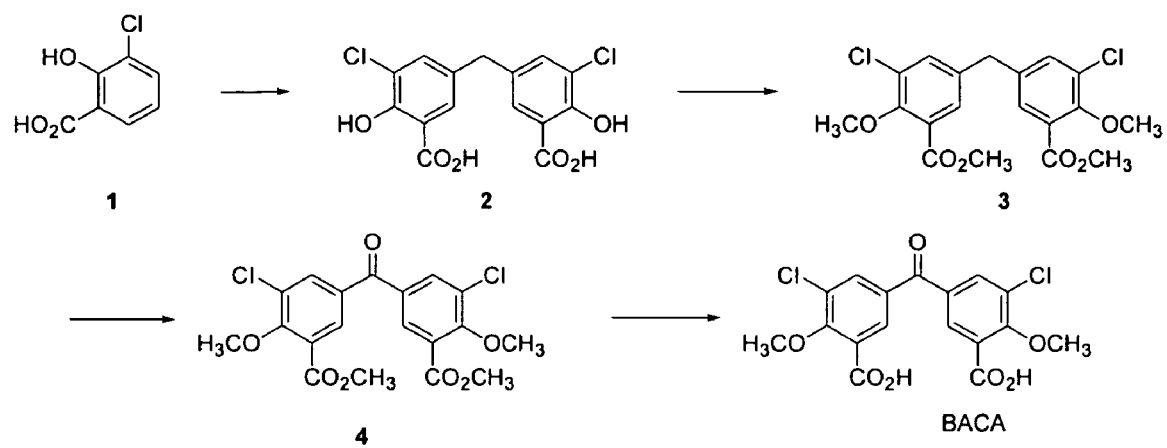
FIG. 2 is a diagram illustrating the synthesis of a BACA.

Synthesis of BACA (FIG. 2)

A suspension of 1 (8.9 g), paraformaldehyde (8.9 g), and $H_2SO_4$ (125 mL) is heated to 90° C. for 14 h and affords crude 2 (7.8 g) after work up. The crude product is 77% pure by HPLC and characterized by $^1$H NMR.

To a solution of 2 (1.0 g) in acetone (30 mL) is added $K_2CO_3$ (3.1 g) and dimethylsulfate (1.4 mL) and the reaction is heated to reflux for 24 h. The reaction is combined with the next batch for work up and purification.

To a solution of 2 (7.5 g) in acetone (225 mL) is added $K_2CO_3$ (23.2 g) and dimethylsulfate (10.8 mL) and the reaction is heated to reflux for 16 h. The reaction, combined with the previous batch, affords 3 (7.3 g, 74%) after work up and column chromatographic purification (ethyl acetate/heptane 1:9). The product is 80% pure by HPLC and characterized by $^1$H NMR.

Chromic anhydride (6.94 g) is added to a suspension of 3 (7.16 g) in acetic anhydride (175 mL) at 3° C. and then stirred at room temperature for 15 h. The reaction affords 4 (5.89 g) after work up and column purification (100% dichloromethane). The product is 90% pure by HPLC and characterized by $^1$H NMR.

To a suspension of 4 (5.89 g) in $THF/H_2O$ (300 mL, 1:1) is added $LiOH\,H_2O$ (1.74 g) at room temperature and the resulting mixture is stirred for 14 h. After an acid/base work up, the product is obtained as a white solid. The product is dried under high vacuum and characterized by nmr and mass spectroscopy.

Example 4

Figure 3:
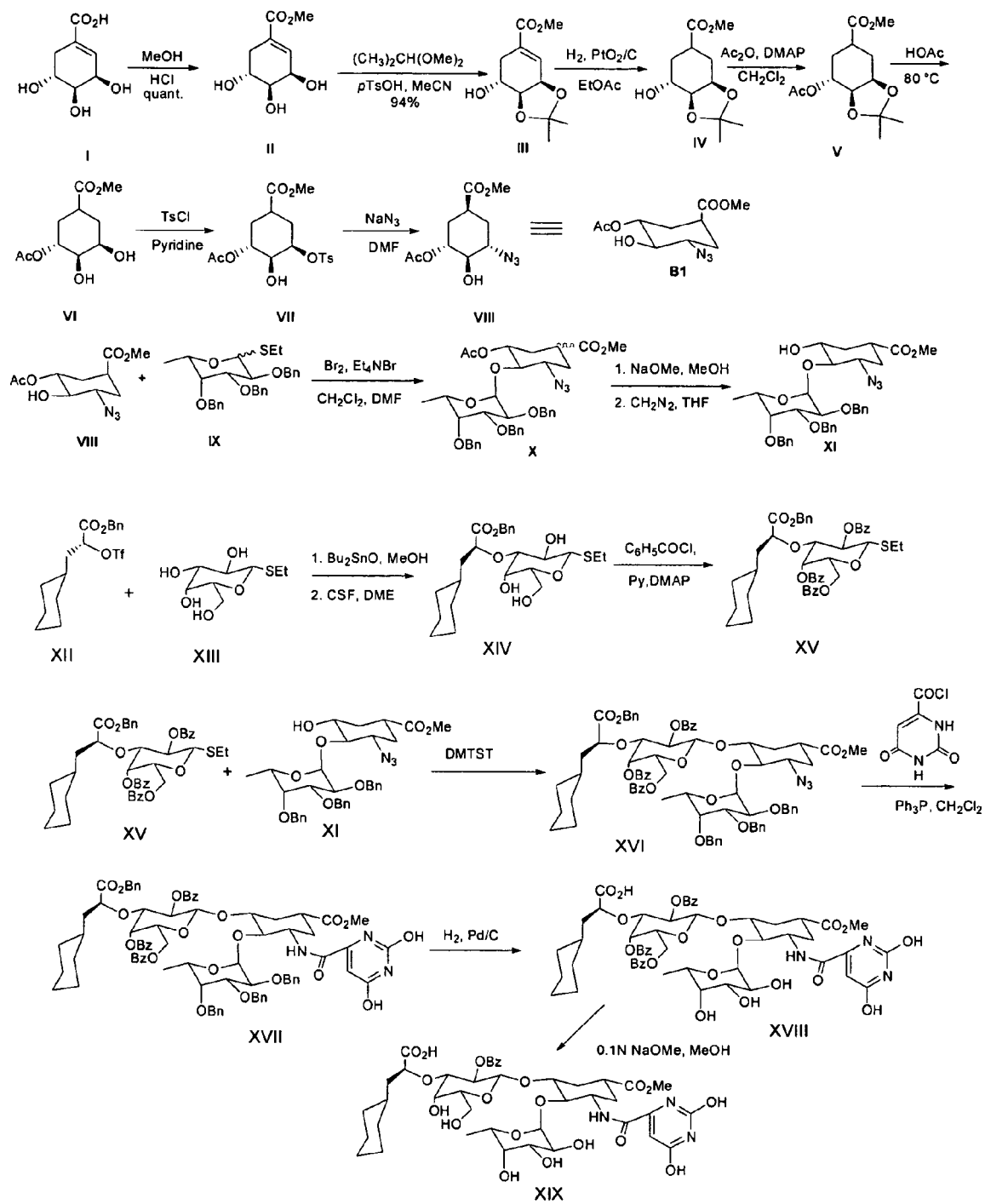
FIG. 3 is a diagram illustrating the synthesis of a glycomimetic (XIX).

Synthesis of Glycomimetic (FIG. 3)

Synthesis of intermediate II: (−)-Shikimic acid (20 g) in MeOH (200 ml) and sulfuric acid (2 ml, 98%) are stirred at rt for 50 h. The reaction mixture is neutralized with 2N aqueous NaOH in the cold. After evaporation to dryness, the residue is purified by silica gel chromatography to afford II (19.2 g).

Synthesis of intermediate (III): Methyl shikimate (II, 10 g), 2,2 dimethoxypropane (10 ml) and p-TsOH (0.8 g) are dissolved in acetonitrile (125 ml) and stirred at rt for 1 h. The reaction mixture is then neutralized with triethylamine (2 ml) and evaporated to dryness. The residue is chromatographed on silica gel to yield III (11 g).

Synthesis of intermediate IV: The shikimic acid derivative III (10 g) and $PtO_2/C$ (10%, 250 mg) in MeOH (40 ml) are hydrogenated at rt under vigorous stirring. After 16 h the reaction mixture is filtered over celite and evaporated to dryness. The residue is chromatographed on silica gel to yield IV.

Synthesis of intermediate V: To a solution of IV (8 g) in DCM (100 ml) at 0° C. are added pyridine (12 ml), acetic anhydride (7 ml) and a DMAP (25 mg). The reaction mixture is stirred at rt for 1 h, and diluted with EtOAc (250 ml). After washing with 0.5 M aqueous HCl (3×50 ml), saturated solution of $KHCO_3$ (3×50 ml) and brine (3×50 ml), the combined organic layers are dried ($Na_2SO_4$) and evaporated to dryness. The residue is purified by chromatography on silica gel to yield V (6.8 g).

Synthesis of intermediate VI: A solution of V (6.0 g) in acetic acid (30 ml, 80%) is stirred at 80° C. for 1 h. Solvent is evaporated off and the residue is purified by chromatography on silica gel (DCM/MeOH 14:1) to yield VI (3.6 g).

Synthesis of intermediate (VII): A solution of VI (3 g) and p-TsCl (3.5 g) in pyridine (30 ml) is stirred at rt for 6 h. MeOH (5 ml) is added and the solvent is evaporated at reduced pressure, the residue dissolved in EtOAc (3×150 ml) and the organic layers are washed with 0.5 M aqueous HCl (0° C.), water (cold) and brine (cold). The combined organic layers are dried ($Na_2SO_4$), filtered on Celite and evaporated to dryness. The residue is purified by chromatography on silica gel (toluene/EtOAc 4:1) to yield VII (3.7 g).

Synthesis of compound VIII: A solution of VII (3 g) and $NaN_3$ (2.5 g) in DMF (20 ml) is stirred at 80° C. The reaction mixture is cooled to rt and diluted with EtOAc (200 ml) and water (50 ml). The organic layer is additionally washed twice with water (2×50 ml) and once with brine (50 ml). All aqueous layers are extracted twice with EtOAc (2×50 ml). The combined organic layers are dried with $Na_2SO_4$, filtered and the solvent is evaporated off. The residue is purified by chromatography on silica gel (petroleum ether/EtOAc 5:2) to give VIII (2.2 g).

Synthesis of compound X: To a solution of ethyl 2,3,4-tri-O-benzyl-α-L-fucothiopyanoside IX (1.5 g) in DCM (3 ml), bromine (150 µl) is added at 0° C. under argon. After 5 min the cooling bath is removed and the reaction mixture is stirred for additional 25 min at rt. Cyclohexene (200 µl) is added and the reaction mixture is added to a solution of VIII (400 mg), $(Et)_4NBr$ (750 mg) and powdered 4 Å molecular sieves in DCM (10 ml) and DMF (5 ml). After 16 h, triethylamine (1.5 ml) is added and stirred for an additional 10 min, diluted with EtOAc (50 ml) and washed with sat. aqueous $NaHCO_3$, water and brine. The aqueous layers are extracted twice with EtOAc (2×50 ml). The combined organic layers are dried ($Na_2SO_4$), filtered and evaporated to dryness. The residue is purified by chromatography on silica gel (toluene/EtOAc 9:1) to yield X (700 mg).

Synthesis of compound XI: To a solution of X (1.5 g) in MeOH (20 ml) is added freshly prepared NaOMe (80 mg) and the reaction mixture is stirred in a pressure tube at 80° C. for 20 h. The reaction mixture is cooled to rt and neutralized with acetic acid. Solvent is evaporated to dryness and the residue is dissolved in ether. Freshly prepared diazomethane is added and the excess diazomethane is neutralized with acetic acid. Solvent is evaporated off to give XI (1.25 g).

Synthesis of building block XV: This synthesis is done exactly in same way as described previously (*Helvetica Chemica Acta* 83:2893-2907 (2000)).

Synthesis of compound XVI: A mixture of XI (1.6 g), XV (3 g) and activated powdered molecular sieves 4 Å (1 g) in DCM (17 ml) is stirred at rt under argon for 2 h. Then DMTST (2 g) is added in 4 equal portions over a period of 1.5 h. After 24 h the reaction mixture is filtered over Celite and the filtrate is diluted with DCM (100 ml). The organic layer is washed with sat. aqueous $NaHCO_3$ and brine and the aqueous layers are extracted twice with DCM. The combined organic layers are dried ($Na_2SO_4$), filtered and evaporated to dryness. The residue is purified by chromatography on silica gel (toluene/EtOAc 8:1) to yield XVI (1.5 g).

Synthesis of compound XVII: To a solution of XVI (500 mg) and orotic acid chloride (500 mg) in dichloromethane (10 ml) is added a solution of triphenylphosphine (500 mg in 5 ml dichloromethane) dropwise during 10 min. The reaction mixture is stirred at rt for 25 h and the solvent is evaporated off. The residue is purified (chromatography on silica gel DCM/MeOH 19:1) to give XVII (250 mg).

Synthesis of compound XVIII: To a solution of XVII (200 mg) in dioxane-water (5:1, 12 ml) is added 10% Pd—C (100 mg) and the reaction mixture is stirred vigorously under hydrogen (55 psi) for 24 h. Catalyst is filtered through a bed of celite and the solvent is evaporated off. Residue is purified by silica gel chromatography to give compound XVIII (150 mg).

Synthesis of XIX: To a solution of compound XVIII (145 mg) in MeOH (5 ml) is added a solution of NaOMe in MeOH (25%, 0.025 ml) and the reaction mixture is stirred at rt for 4 h, neutralized with acetic acid and the solvent is evaporated off. Residue is dissolved in water and passed through a bed of Dowex 50wX-8 (Na-form) resin. Water wash is evaporated off to afford compound XIX (100 mg).

Synthesis of EDA-XIX: XIX (80 mg) is heated at 70° C. with ethylenediamine (EDA) (1 ml) with stirring for 5 h. Solvent is evaporated off and the purified by sephadex G-25 column to give EDA-XIX (82 mg).

Example 5

Figure 4:
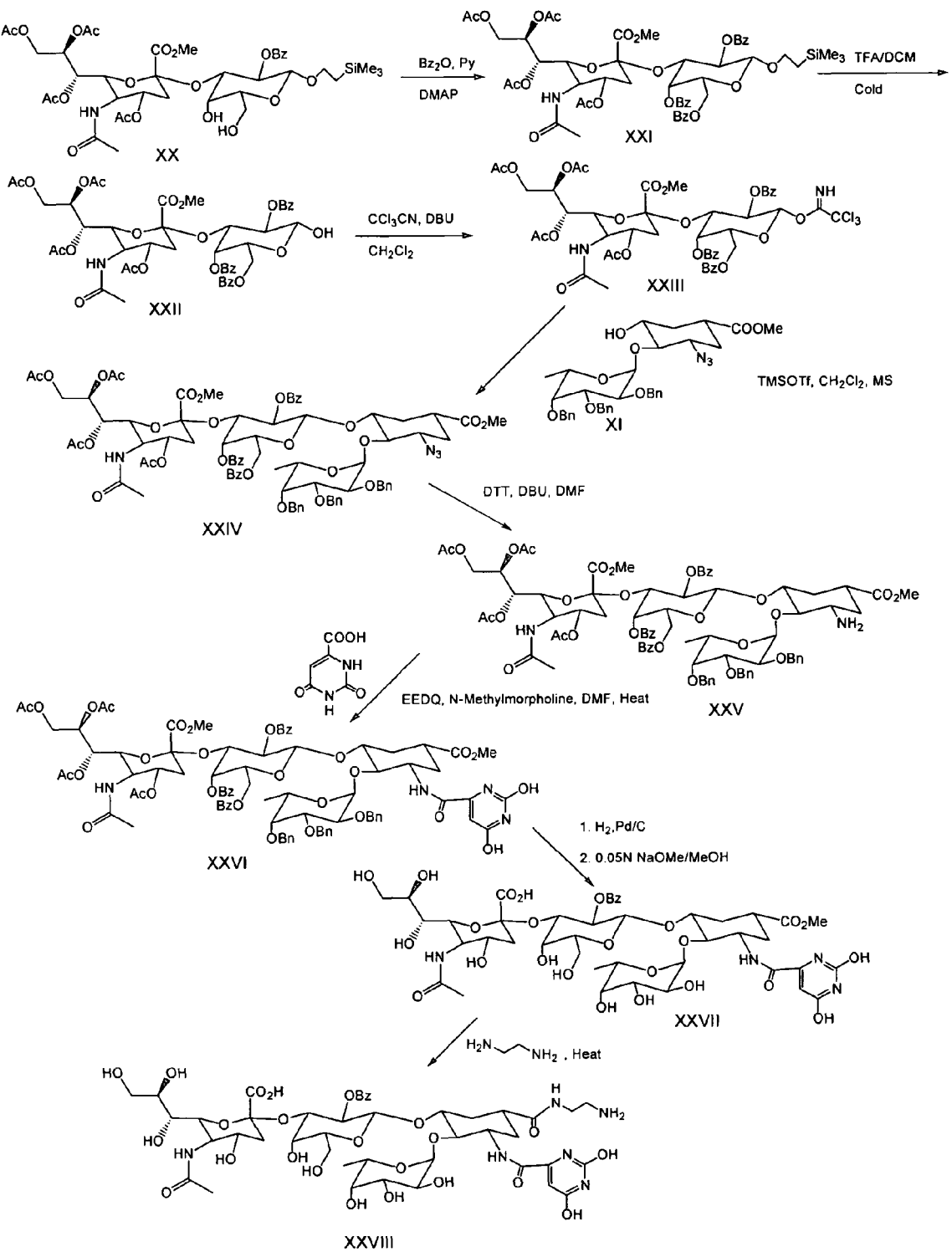
FIG. 4 is a diagram illustrating the synthesis of a glycomimetic (XXVIII).
Figure 5:
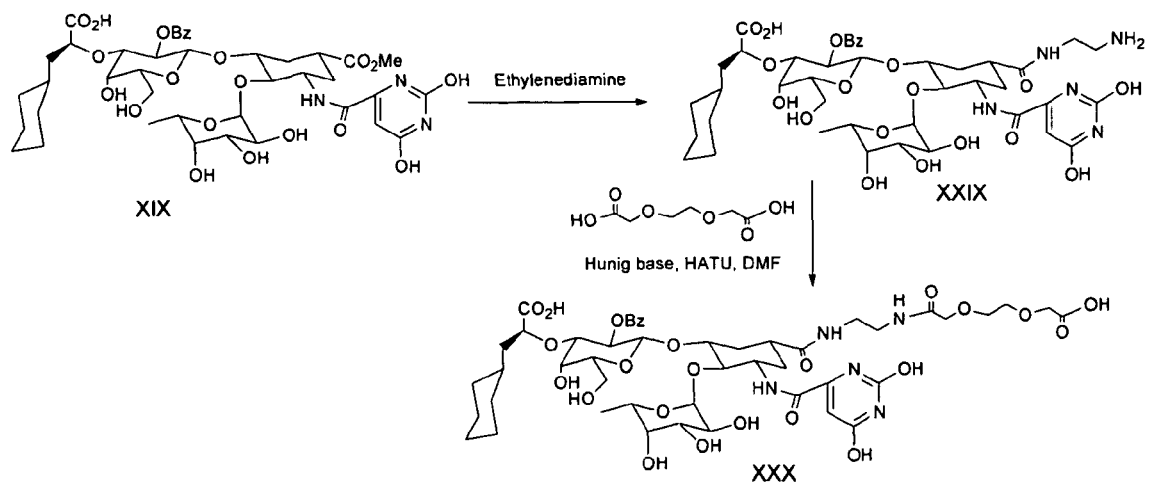
FIG. 5 is a diagram illustrating the synthesis of a PEGylated glycomimetic (XXX).
Figure 6:
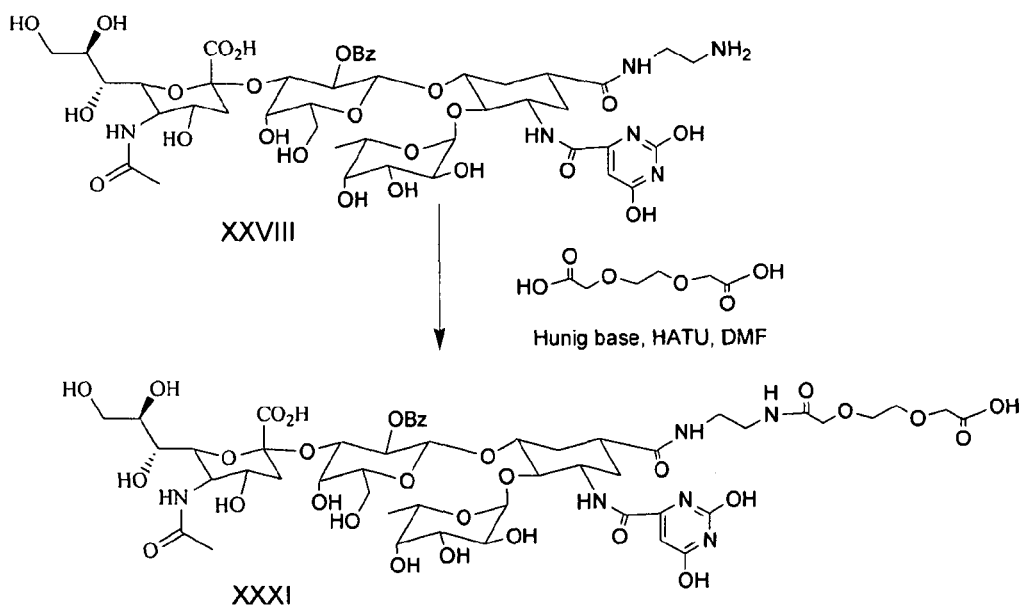
FIG. 6 is a diagram illustrating the synthesis of a PEGylated glycomimetic (XXXI).

Synthesis of Glycomimetic (FIG. 4)

Synthesis of compound XXI: To a solution of compound XX (1.5 g, synthesized according to previously published procedure Carbohydrate Chemistry and Biochemistry, 2000, vol. 1, page 345-365) in pyridine (60 ml) is added benzoic anhydride (0.73 g) and dimethyl amino pyridine (0.02 g). The reaction mixture is stirred at room temperature for 20 h. Solvent is evaporated off and the residue is dissolved in dichloromethane. The solution is washed successively with cold 1N HCl and water. The solution is dried (sodium sulfate) and concentrated to dryness. Residue is purified by column chromatography (silica gel) to give compound XXI (1 g).

Synthesis of compound XXII: To a solution of compound XXI in dichloromethane (20 ml) is added trifluoroacetic acid (20 ml) at 0° C. and the reaction mixture is stirred at the same temperature for 1 h. Solvent is evaporated off and the residue is purified by column chromatography (silica gel) to give compound XXII (0.6 g).

Synthesis of compound XXIII: To a solution of compound XXII (1 g) in dichloromethane (40 ml) is added DBU (0.05 ml) and tricholroacetonitrile (0.4 g) at 0° C. The solution is stirred at the same temperature for 1.5 h. Solvent is evaporated off and purified by column chromatography (silica gel) to give compound XXIII (0.6 g).

Synthesis of compound XXIV: To a mixture of compound XI (0.7 g), compound XXIII (0.5 g) in dichloromethane (40 ml) and molecular sieves (4 Å, 5 g) is added a solution of TMSOTf (0.15 ml in dichloromethane (5 ml)) dropwise at 0° C. with stirring. Stirring is continued at the same temperature for 2 h. Triethylamine (0.2 ml) is added and the reaction mixture is filtered through a bed of celite. Reaction mixture is washed with cold saturated solution of sodium bicarbonate and water. Dried (sodium sulfate) and concentrated to dryness. The residue is purified by column chromatography (silica gel) to give compound XXIV (0.7 g).

Synthesis of compound XXV: To a solution of compound XXIV (0.6 g) in DMF (30 ml) is added DBU (30 drops) and dl-dithio-threitol (DTT, 0.28 g). The reaction mixture is stirred at room temperature for 1 h. Solvent is evaporated off, residue is dissolved in dichloromethane and washed with water. Organic layer is dried (sodium sulfate) and concentrated to dryness. The residue is purified by column chromatography (silica gel) to give compound XXV (0.45 g).

Synthesis of compound XXVI: To a solution of compound XXV (0.4 g) in DMF (10 ml) is added orotic acid (0.14 g), EEDQ (0.19 g), 4-methyl-morpholine (0.09 g) and the reaction mixture is stirred at 70° C. for 20 h. Solvent is evaporated off and residue is dissolved in dichloromethane. The solution is washed with cold saturated sodium bicarbonate solution and water. Organic layer is dried (sodium sulfate) and concentrated to dryness. The residue is purified by column chromatography (silica gel) to give compound XXVI (0.2 g).

Synthesis of compound XXVII: Compound XXVII (0.2 g) is hydrogenated exactly in the same condition as described and the intermediate is partially debenzoylated using NaOMe in MeOH as described to give compound XXVII (0.050 g) after chromatographic purification.

Synthesis of compound XXVIII: Compound XXVII is treated with ethylenediamine as described and purified by column chromatography (silica gel and gel filtration sephadex G-25) to give compound XXVIII (25 mg).

Example 6

Figure 7A:
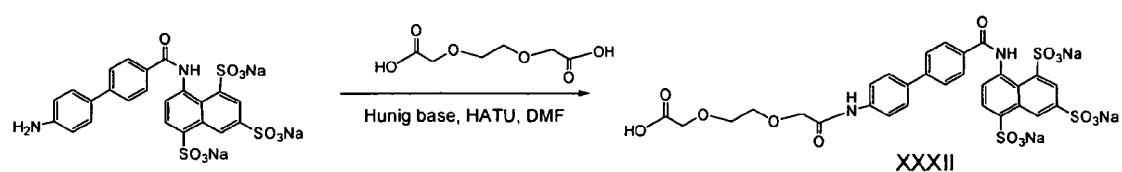
FIGS. 7A, 7B, and 7C are diagrams illustrating the syntheses of PEGylated BASAs (XXXII and XXXIII) and PEGylated BACAs (XXXVI and XXXVIa).
Figure 7B:
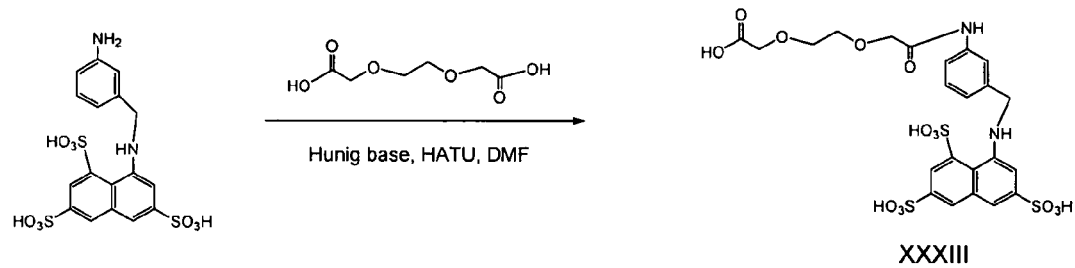

Synthesis of PEGylated BASA (FIG. 7B)

To a solution of 3,6-dioxaoctanedioic acid (PEG, 200 mg, available commercially) in DMF (1 ml) is added Hunig base (0.4 ml), and then HATU (0.35 g) is added after 5 min. The solution is stirred at RT for 10 min. and then a solution of the BASA of Example 2 (50 mg) in DMF (0.1 ml) is added. The reaction mixture is stirred for 4 h at rt and the solvent is evaporated off. The residue is purified by hpic (reverse-phase C18 column) to give XXXIII (40 mg).

Example 7

Synthesis of PEGylated BASA (FIG. 7A)

This synthesis is performed in the same way as described in Example 6, except using the BASA of Example 1 to give XXXII (50 mg).

Example 8

Figure 7C:
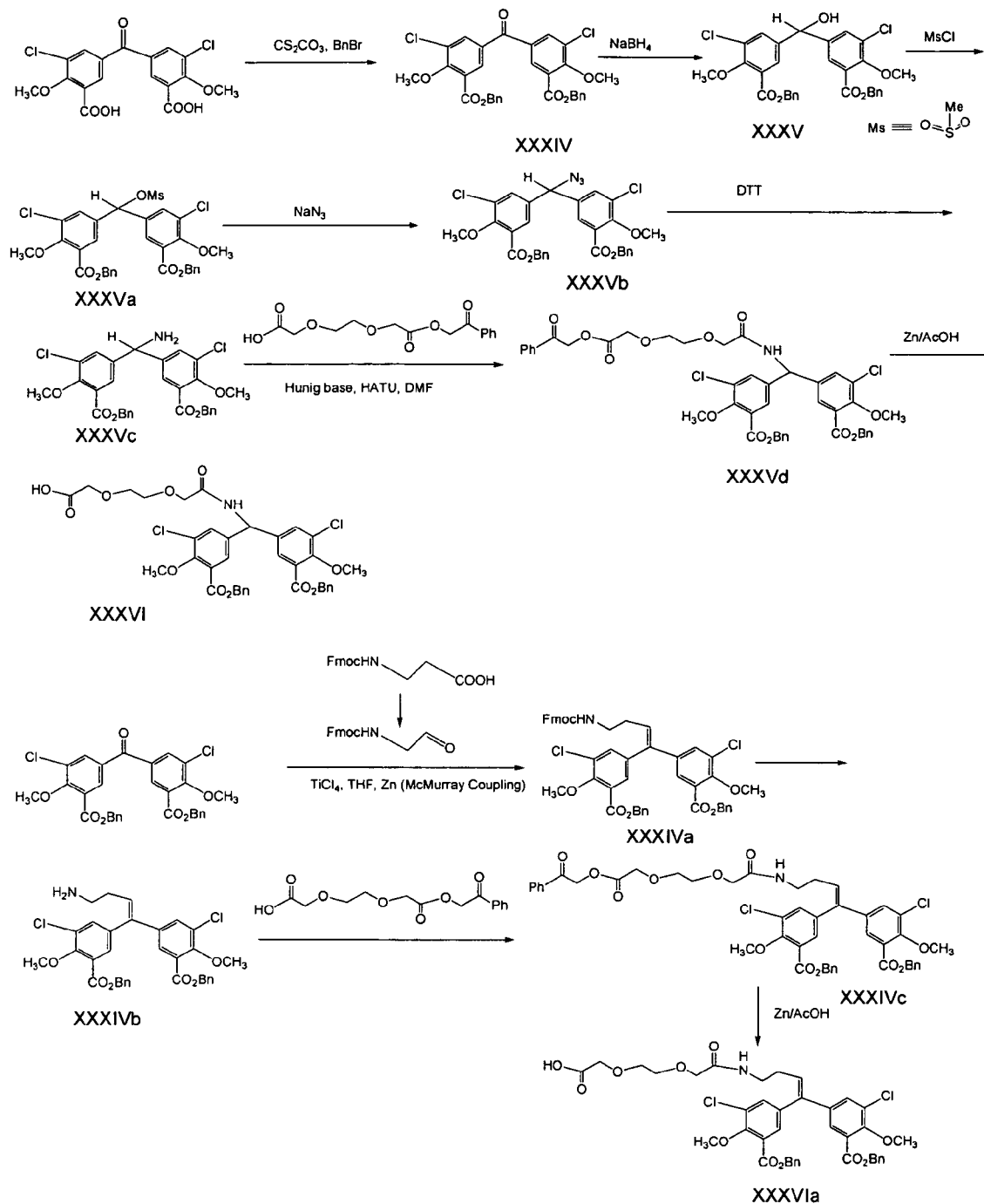

Synthesis of PEGylated BACA (FIG. 7C)

Synthesis of intermediate XXXIV (Method 1): The BACA of Example 3 (0.5 g) is suspended in methanol-water (1 ml, 9:1) and the pH is adjusted to 8.2 by the addition of an aqueous solution of $Cs_2CO_3$. The solvent is removed and then coevaporated with toluene. The residue is dissolved in DMF (1 ml). Benzylbromide (0.5 ml) is added and stirred for 20 h at room temperature. Dichloromethane (15 ml) is added washed with cold water. Organic layer is dried (anhydrous sodium sulfate) and solvent is evaporated off. The residue is purified by column chromatography (silica) to give XXXIV (0.48 g).

Synthesis of intermediate XXXIV (Method 2): To a solution of the BACA of Example 3 (1 g) in DMF is added N,N-diisopropyl ethylamine (1.5 g) and Benzylbromide (1.5 g). The reaction mixture is stirred at 50° C. for 20 h. Solvent is evaporated off and the residue is purified by column chromatography (silica) to give XXXIV.

Synthesis of intermediate of XXXV: To a solution of XXXIV (0.2 g) in MeOH (10 ml) is added sodiumborohydride (0.070 g) at 0° C. and the reaction mixture is stirred at 0° C. for 1 h. The reaction is quenched by addition of acetic acid and concentrated to dryness. Residue is purified column chromatography (silica) to afford XXXV (0.16 g).

Synthesis of intermediate of XXXVb: To a solution of XXXV (0.36 g) in dichloromethane is added triethylamine (0.6 ml) and $MeSO_2Cl$ (0.29 ml). The reaction mixture is stirred at RT for 21 h. Reaction mixture is diluted with dichloromethane, washed with water, 1 M HCl, and brine. Organic layer is dried ($Na_2SO_4$) and concentrated to dryness to give crude XXXVa. To a solution of crude XXXVa in DMF (5 ml) is added $NaN_3$ (0.18 g). The reaction mixture is stirred at 100° C. for 4 h and the solvent is evaporated off. The residue is dissolved in $CH_2Cl_2$ and washed with cold brine, cold 1 M HCl, cold $NaHCO_3$ solution, and cold water. Organic layer is dried ($Na_2SO_4$) and concentrated to dryness. The residue is purified by column chromatography (silica) to give XXXVb (0.14 g).

Synthesis of intermediate XXXVc: To a solution of XXXVc (0.08 g) in DMF (3 ml) is added DTT (0.04 g) and DBU (0.02 ml) and stirred at RT for 1 h. Solvent is evaporated off and the residue is dissolved in EtOAc, washed with $H_2O$ and the organic layer is concentrated to dryness. The residue is purified by column chromatography (silica) to afford intermediate XXXVc (0.061 g).

Synthesis of intermediate XXXVd: To a solution of monoprotected PEG-dicarboxylic acid (0.6 g) in DMF (3 ml) is added diisopropylethylamine (0.24 ml) and HATU (0.513 g) with stirring. A solution of intermediate XXXVc (0.185 g) in DMF (3 ml) is added into the above solution. The reaction mixture is stirred at RT for 1 h. Solvent is evaporated off and the residue is dissolved in EtOAc. EtOAc layer is washed with water and purified by column chromatography to give intermediate XXXVd.

Synthesis of XXXVI: To a solution of XXXVd (0.185 g) in glacial AcOH (3 ml) is added Zn dust (0.1 g) and the reaction is stirred at 40° C. for 30 min. Reaction mixture is filtered through a celite bed and Zn cake is washed with MeOH. The filtrate is concentrated to dryness and purified by sep-pak C18 column to afford XXXVI (0.050 g).

Synthesis of intermediate XXXIVa: A suspension of $TiCl_4$-Tetrahydrofuran complex (0.705 g) and Zn-dust (0.28 g) in THF (25 ml) is refluxed for 2 h at 75° C. for 2 h with stirring under inert atmosphere. To this mixture is added a solution of the BACA of Example 3 (0.3 g) and N-fluorenylmethoxycarbonyl-3-aminopropanol (0.312 g, prepared as described in the literature Casimiro-Garcia et al, Bioorg. Med. Chem., 1979 (2001) 2827). The reaction mixture is stirred at 75° C. for 2.5 h (McMurray coupling) under inert atmosphere. The reaction is cooled down to RT and $H_2O$ (30 ml) is added, filtered through a celite bed and the filtrate is washed three times with EtOAc (30 ml each). Organic layer is collected together and dried ($Na_2SO_4$), filtered and concentrated to dryness. Residue is purified by column chromatography to yield XXXIVa.

Synthesis of intermediate XXXIVb: To a solution of XXXIVa (0.444 g) in anhydrous THF (21 ml) is added piperidine (6.25 ml) and the reaction mixture is stirred at RT for 3 h. The solvent is evaporated off and the residue is purified by column chromatography (silica) to give intermediate XXXIVb (0.26 g).

Solid phase synthesis of intermediate XXXIVc: A mixture of PS-Carbodiimide resin (0.200 g), HOBt (0.030 g), and mono protected PEG-COOH (0.080 g) in $CH_2Cl_2$ (3 ml) is stirred for 5 min at RT in a syringe reactor. To the above mixture is added a solution of intermediate XXXIVb (0.080 g) in $CH_2Cl_2$ (3 ml) and the reaction mixture is stirred at RT for 3 h. MP-carbonate resin (0.216 g) is added and stirred for 2 h at RT. Resin is filtered off and then the resin is washed 5 times with $CH_2Cl_2$. Filtrate is combined and concentrated to dryness to afford intermediate XXXIVc.

Synthesis of Intermediate XXXVIa: XXXIVc (0.12 g) is treated with Zn/AcOH exactly in the same as described for the synthesis of intermediate XXXVI to yield intermediate XXXVIa (0.104 g).

Example 9

Synthesis of PEGylated BACA (FIG. 7C)

Synthesis of Intermediate XXXIVa: A suspension of $TiCl_4$-Tetrahydrofuran complex (0.705 g) and Zn-dust (0.28 g) in THF (25 ml) is refluxed for 2 h at 75° C. for 2 h with stirring under inert atmosphere. To this mixture is added a solution of the BACA of Example 3 (0.3 g) and N-fluorenylmethoxycarbonyl-3-aminopropanol (0.312 g, prepared as described in the literature Casimiro-Garcia et al, Bioorg. Med. Chem., 1979 (2001) 2827). The reaction mixture is stirred at 75° C. for 2.5 h (McMurray coupling) under inert atmosphere. The reaction is cooled down to RT and $H_2O$ (30 ml) is added, filtered through a celite bed and the filtrate is washed three times with EtOAc (30 ml each). Organic layer is collected together and dried ($Na_2SO_4$), filtered and concentrated to dryness. Residue is purified by column chromatography to yield XXXIVa.

Synthesis of intermediate XXXIVb: To a solution of XXXIVa (0.444 g) in anhydrous THF (21 ml) is added piperidine (6.25 ml) and the reaction mixture is stirred at RT for 3 h. The solvent is evaporated off and the residue is purified by column chromatography (silica) to give intermediate XXXIVb (0.26 g).

Solid phase synthesis of intermediate XXXIVc: A mixture of PS-Carbodiimide resin (0.200 g), HOBt (0.030 g), and mono protected PEG-COOH (0.080 g) in $CH_2Cl_2$ (3 ml) is stirred for 5 min at RT in a syringe reactor. To the above mixture is added a solution of intermediate XXXIVb (0.080 g) in $CH_2Cl_2$ (3 ml) and the reaction mixture is stirred at RT for 3 h. MP-carbonate resin (0.216 g) is added and stirred for 2 h at RT. Resin is filtered off and then the resin is washed 5 times with $CH_2Cl_2$. Filtrate is combined and concentrated to dryness to afford intermediate XXXIVc.

Synthesis of XXXVIa: XXXIVc (0.12 g) is treated with Zn/AcOH exactly in the same as described for the synthesis of intermediate XXXVI to yield intermediate XXXVIa (0.104 g).

Example 10

Figure 8A:
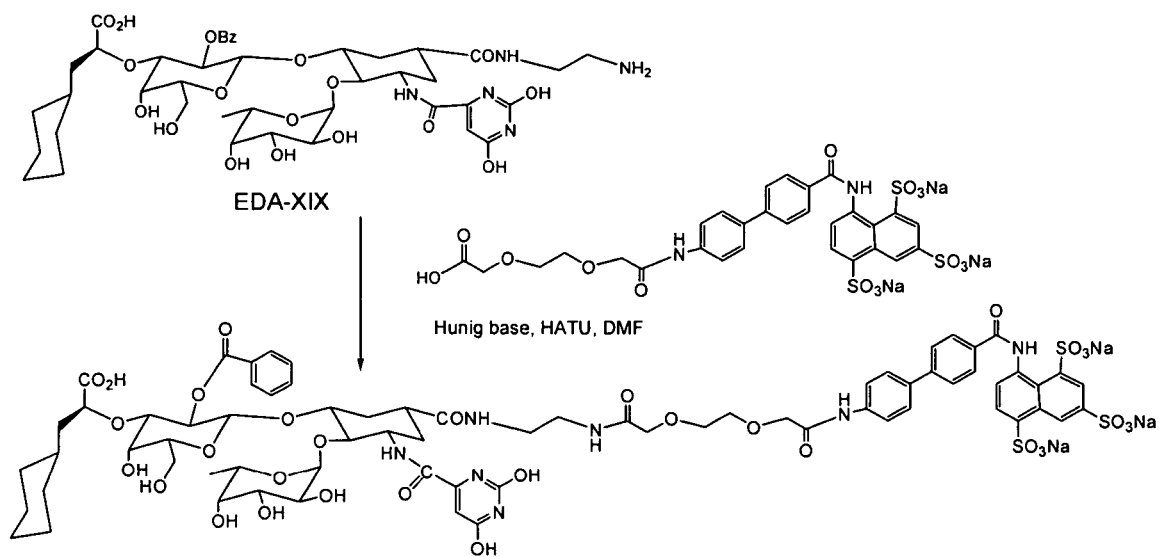
FIGS. 8A, 8B and 8C are diagrams illustrating the syntheses of Glycomimetic-BASA (FIGS. 8A and 8C) and Glycomimetic-BACA (FIG. 8B).

Synthesis of Glycomimetic-BASA (FIG. 8A)

To a solution of XXXII from Example 7 (0.015 g) in DMF (0.1 ml) is added Hunig base (0.015 ml) and then HATU (0.007 g). The reaction mixture is stirred for 10 min at RT. A solution of EDA-XIX from Example 4 (0.010 g in DMF ml) is added and the reaction mixture is stirred at RT for 8 h. Solvent is evaporated off and the residue is purified by sephadex G-25 chromatography to give Glycomimetic-BASA of FIG. 8A (0.008 g).

Example 11

Figure 8B:
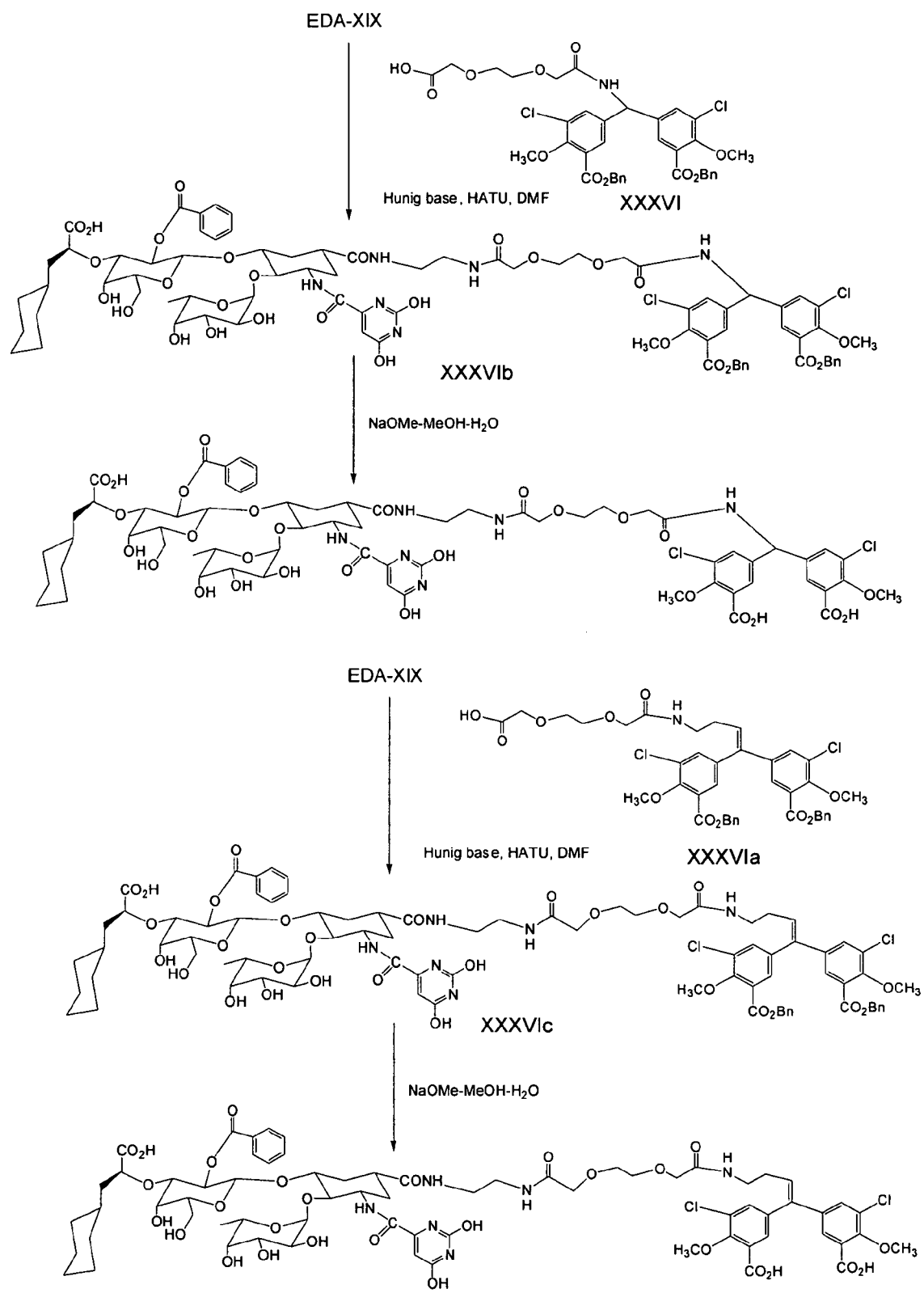

Synthesis of Glycomimetic-BACA (FIG. 8B)

Coupling between EDA-XIX and XXXVI: To a solution of XXXVI from Example 8 in DMF is added diisopropylethylamine and then HATU. The solution is stirred for 3 min at RT. The above solution is then added to EDA-XIX with stirring in a conical vial. Reaction mixture is stirred for 2 h at RT. Solvent is evaporated off to give crude intermediate XXXVIb and is used for the next step without further purification.

The crude XXXVIb is treated with NaOMe-MeOH—$H_2O$ for 2 h and then purified by gel filtration to give a Glycomimetic-BACA.

Coupling between EDA-XIX and XXXVIa from Example 9: This coupling reaction is performed exactly in the same way as described for the synthesis of XXXVIb to give crude product XXXVIc.

XXXVIc is treated with NaOMe-MeOH—$H_2O$ exactly in the same way as described to afford a Glycomimetic-BACA.

Example 12

Figure 8C:
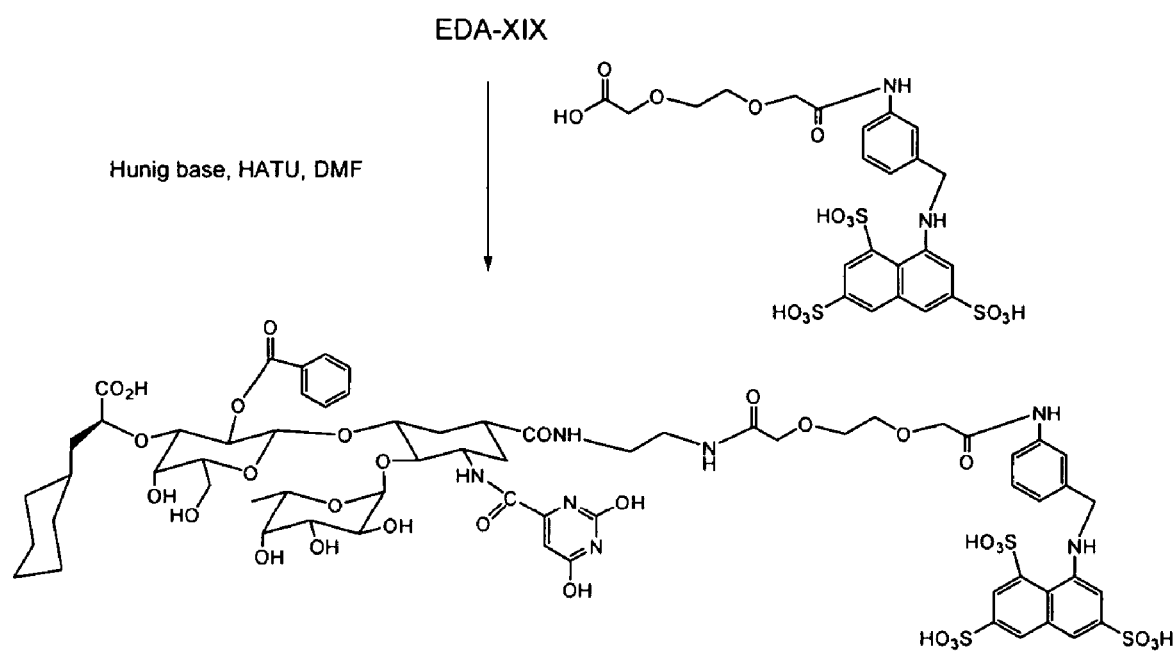

Synthesis of Glycomimetic-BASA (FIG. 8C)

This synthesis is performed in the same way as described in Example 10 using XXXIII from Example 6 and EDA-XIX from Example 4 to give Glycomimetic-BASA of FIG. 8C. Alternatively, XXXIII can be replaced with XLV from Example 18 for reaction with EDA-XIX.

Example 13

Figure 9A:
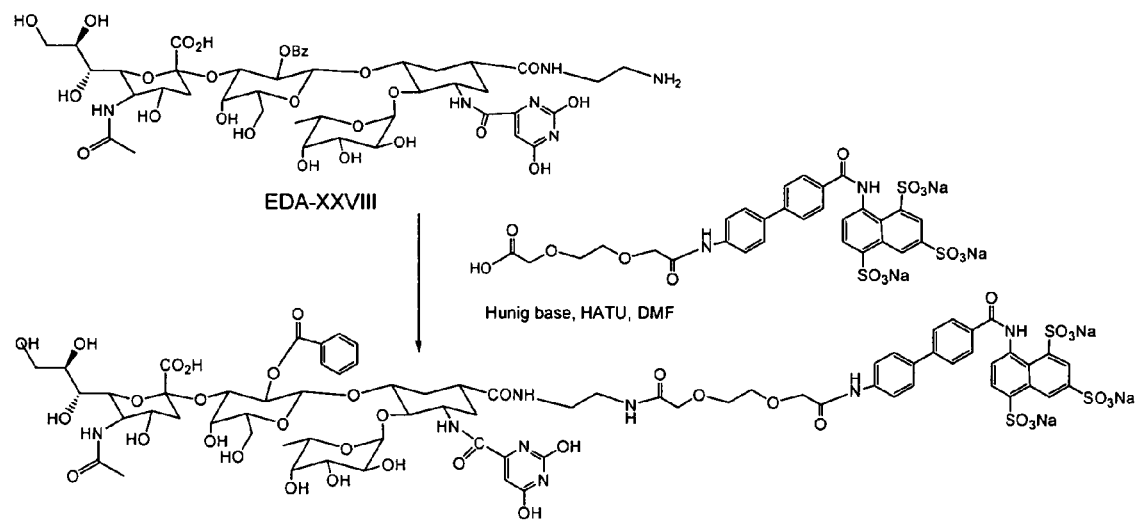
FIGS. 9A, 9B and 9C are diagrams illustrating the syntheses of Glycomimetic-BASA (FIGS. 9A and 9C) and Glycomimetic-BACA (FIG. 9B).

Synthesis of Glycomimetic-BASA (FIG. 9A)

This synthesis is performed in the same way as described in Example 10 using XXXII from Example 7 and EDA-XXVIII from Example 5 to give Glycomimetic-BASA of FIG. 9A.

Example 14

Figure 9B:
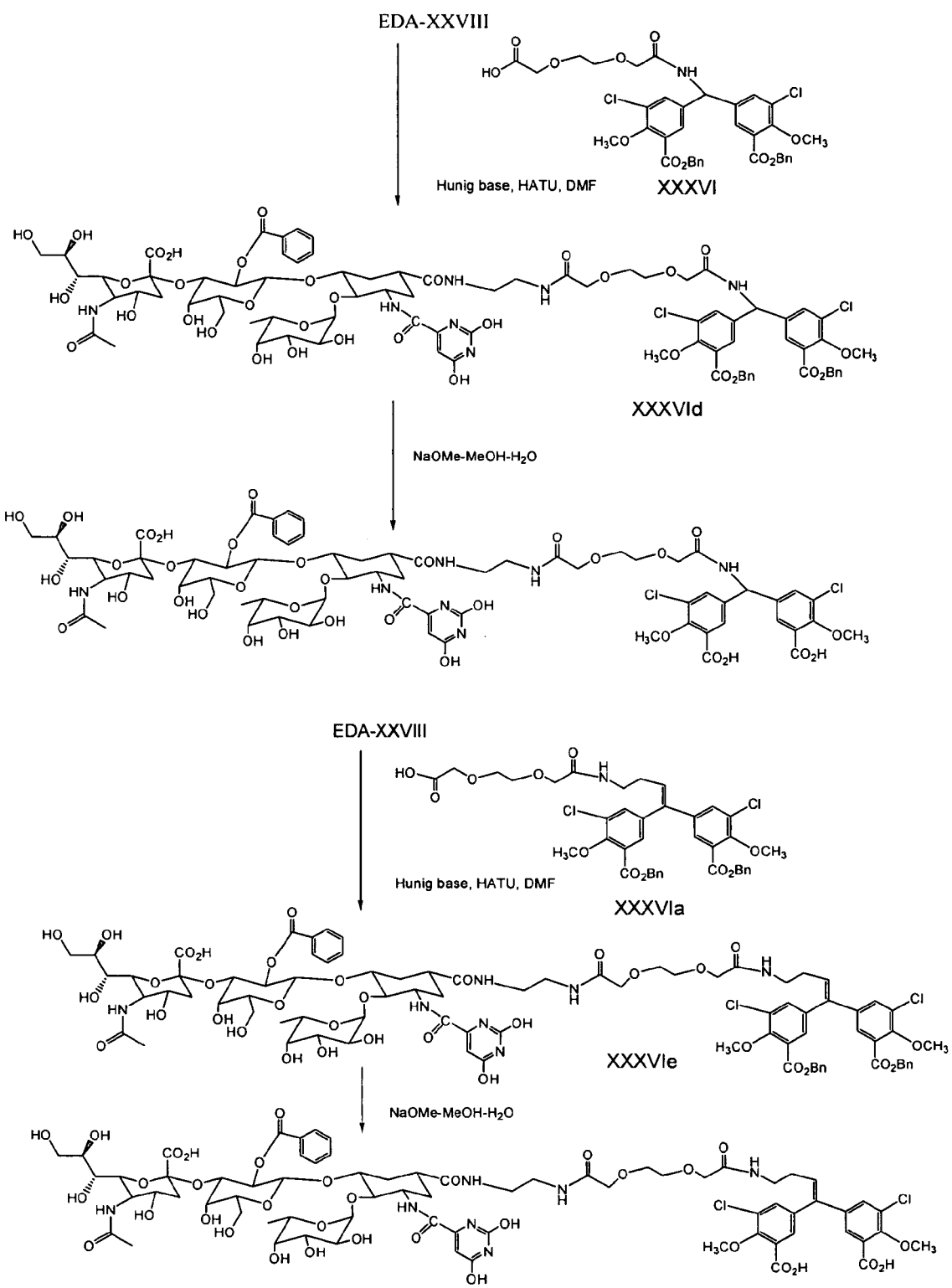

Synthesis of Glycomimetic-BACA (FIG. 9B)

Coupling between EDA-XXVIII and XXXVI: This coupling reaction is performed exactly in the same way as described for the synthesis of XXXVIb to give crude product XXXVId.

XXXVId is treated with NaOMe-MeOH—$H_2O$ exactly in the same way as described to afford a Glycomimetic-BACA.

Coupling between EDA-XXVIII and XXXVIa: This coupling reaction is performed exactly in the same way as described for the synthesis of XXXVIb to give crude product XXXVIe.

XXXVIe is treated with NaOMe-MeOH-$H_2O$ exactly in the same way as described to afford a Glycomimetic-BACA.

Example 15

Figure 9C:
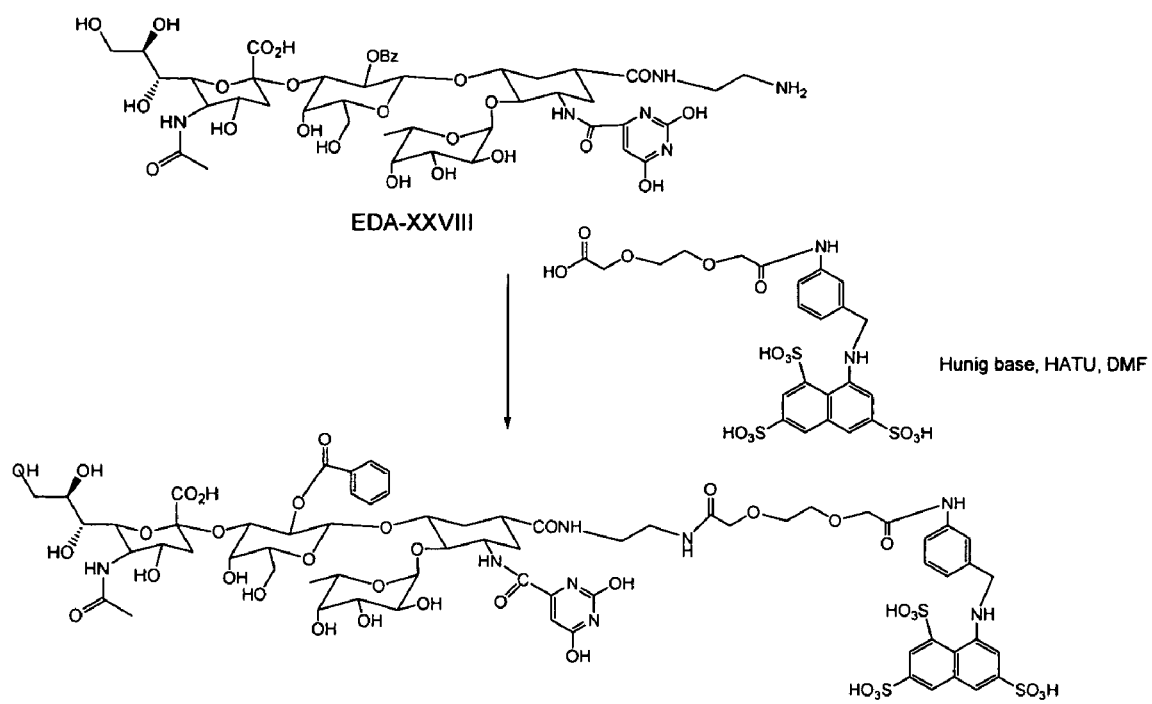
Figure 10:
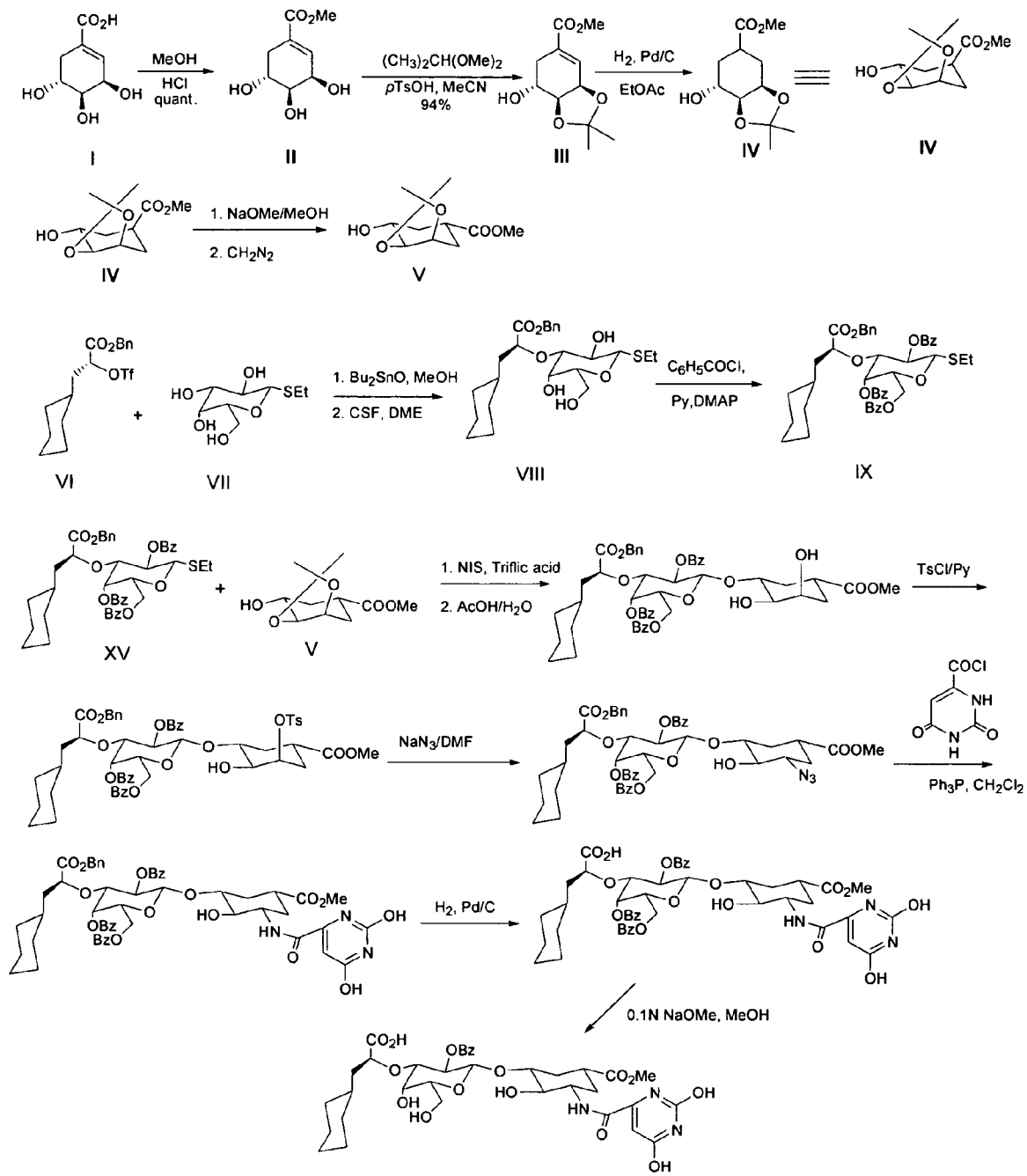
FIG. 10 is a diagram illustrating the synthesis of a glycomimetic.
Figure 11:
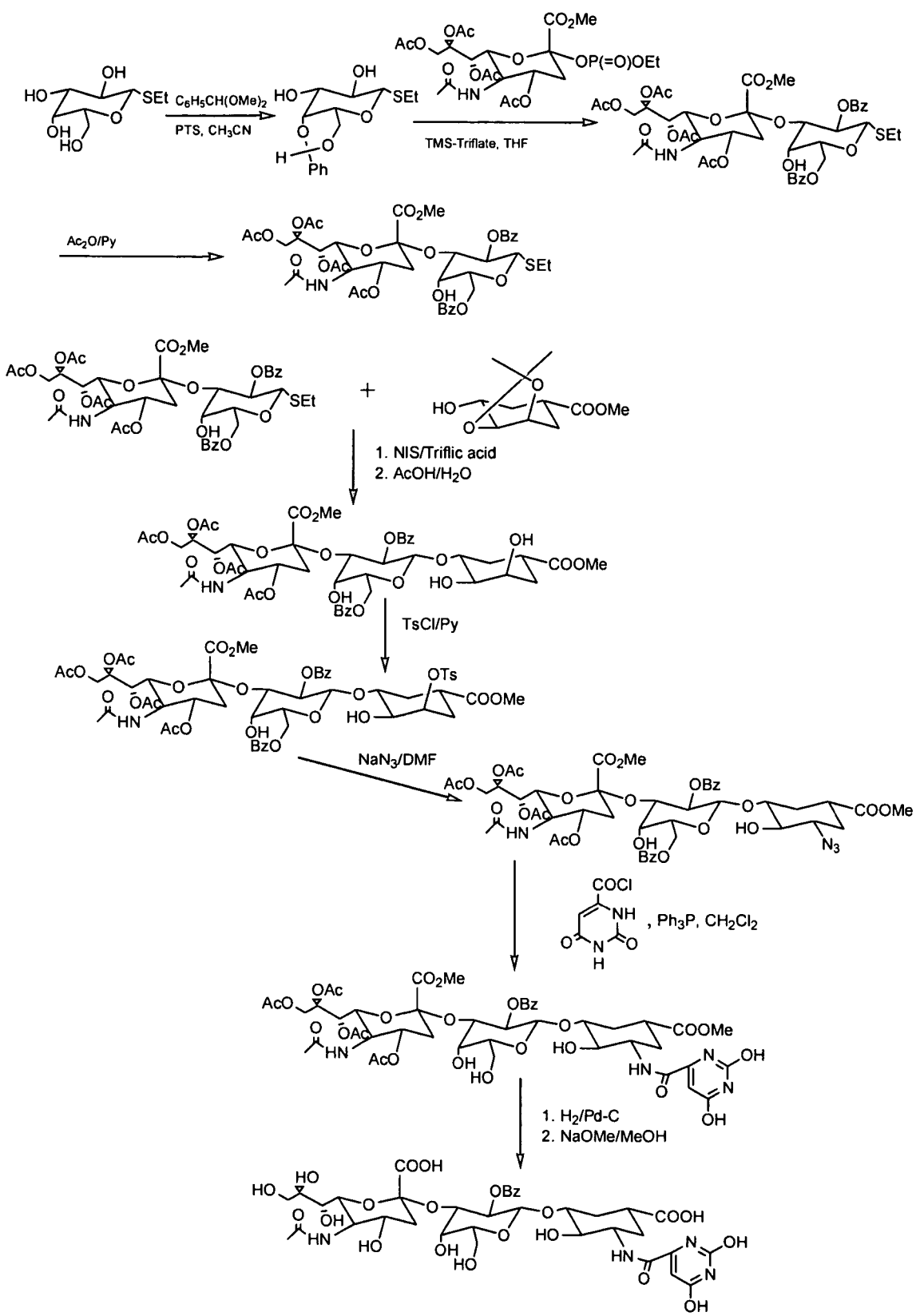
FIG. 11 is a diagram illustrating the synthesis of a glycomimetic.

Synthesis of Glycomimetic-BASA (FIG. 9C)

This synthesis is performed in the same way as described in Example 10 using XXXIII from Example 6 and EDA-XXVIII from Example 5 to give Glycomimetic-BASA of FIG. 9C. Alternatively, XXXIII can be replaced with XLV from Example 18 for reaction with EDA-XXVIII.

Example 16

Figure 12:
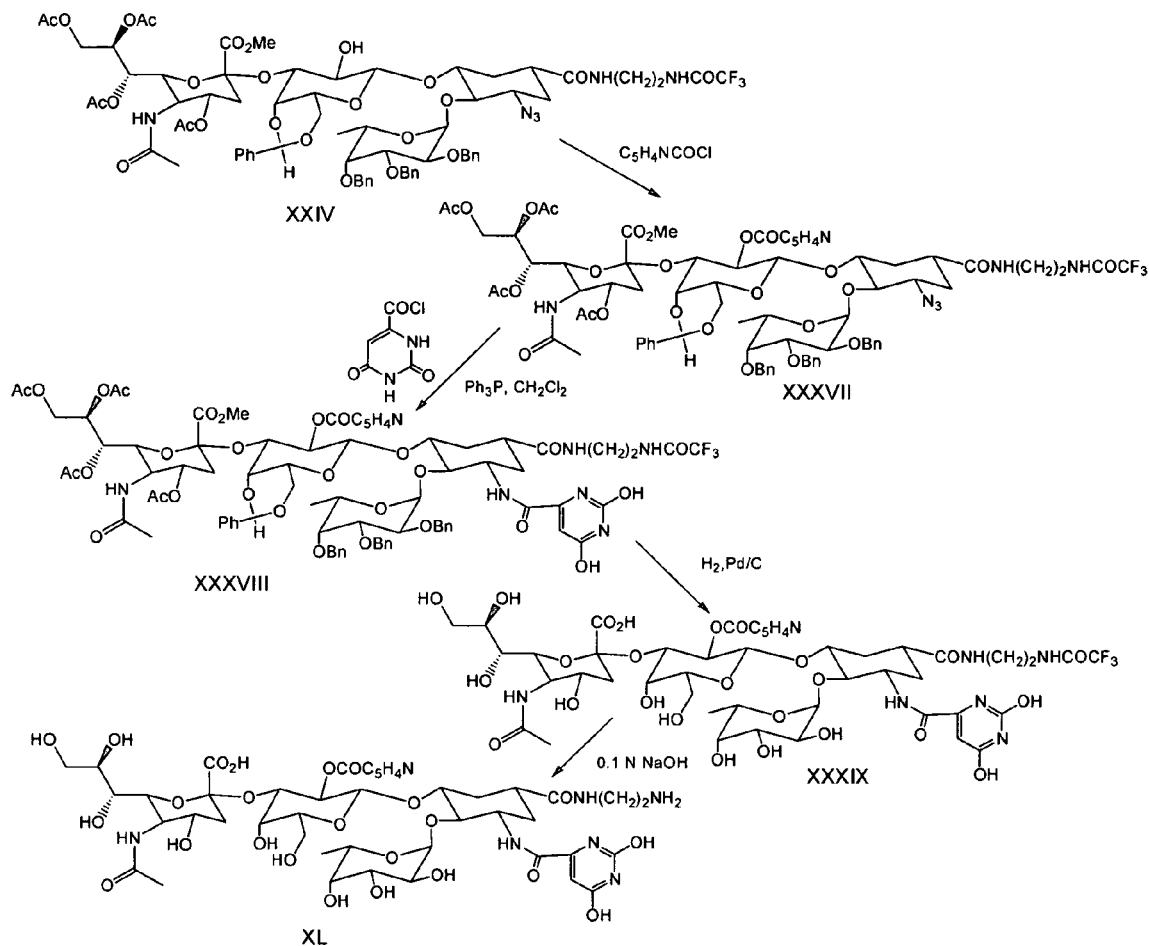
FIG. 12 is a diagram illustrating the synthesis of a glycomimetic.

Synthesis of Glycomimetic (FIG. 12)

Synthesis of intermediate XXXVII: A solution of intermediate XXIV (0.1 g) from Example 5 in pyridine is treated with nicotinyl chloride (0.08 ml) in pyridine and dimethylaminopyridine (0.04 g) in the same way as described in Example 5 for the synthesis of intermediate XXV to give intermediate XXXVII (0.075 g).

Synthesis of intermediate XXXVIII: Intermediate XXXVII (0.07 g) is treated with triphenylphosphine and orotic acid chloride in the same way as described in Example 4 for the synthesis of compound XVII to give XXXVIII (0.048 g).

Synthesis of intermediate XXXIX: Hydrogenation of intermediate XXXVIII (0.04 g) with Pd/C as described gives compound XXXIX (0.02 g).

Synthesis of Compound XL: Intermediate XXXIX (0.015 g) is treated with 0.5N NaOH for 10 min at 60° C. to afford compound XL (0.010 g) after purification by sephadex G-25 gel filtration.

Example 17

Figure 13:
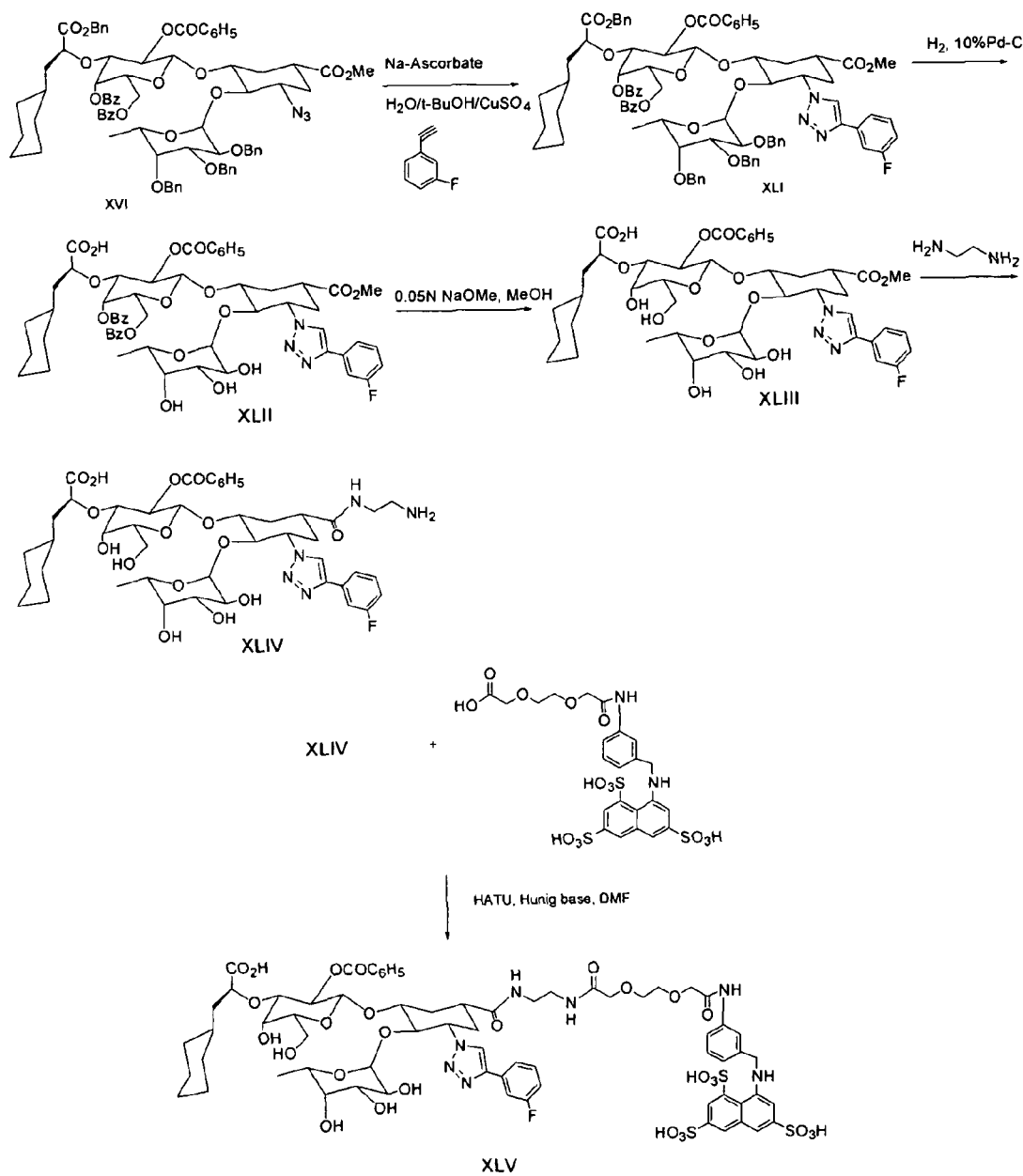
FIG. 13 is a diagram illustrating the synthesis of a glycomimetic-BASA.

Synthesis of Glycomimetic (FIG. 13)

Synthesis of XLI: To a suspension of compound XVI (0.1 g) in t-BuOH-water (4ml, 1:1) is added 1-ethynyl-3-fluorobenzene (0.9 g), 1% $CuSO4$ (0.1 ml), and Na-I-ascorbate (4 mg). The mixture is heated (70° C.) with stirring for 20 h. Solvent is evaporated off and the residue is dissolved in dichloromethane. Organic layer is washed with water dried (anhydrous sodium sulfate) and concentrated to dryness. The residue is purified by column chromatography (silica gel) to give compound XLI (0.08 g).

Synthesis of XLII: Compound XLI (0.25 g) is dissolved in dioxane-water (4:1, 7.5 ml). 10% Pd-C (0.25 g) is added, followed by AcOH (7 drops). The mixture is hydrogenated for 15 h at 40 psi. The reaction mixture is filtered through a celite bed and concentrated to dryness to give compound XLII (0.2 g).

Synthesis of XLIII: To a solution of compound XLII (0.2 g) in MeOH (5 ml) is added a solution of NaOMe in MeOH (0.05 ml) and the reaction mixture is stirred at room temperature for 2 h. The reaction mixture is neutralized with few drops of acetic acid and concentrated to dryness. Residue is purified by column chromatography (silica gel) to give compound XLIII (0.15 g).

Synthesis of XLIV: Compound XLIII (0.15 g) is dissolved in ethylenediamine (7 ml) and the reaction mixture is stirred at 70° C. for 9 h. Solvent is evaporated off and the residue is first purified by column chromatography (silica gel) and then by reverse phase C18 to give compound XLIV (0.11 g).

Synthesis of Glycomimetic-BASA (compound XLV): This synthesis is performed in the same way as described in example 10 using XXXIII from example 6 and XLIV to give compound XLV.

Example 18

Figure 14:
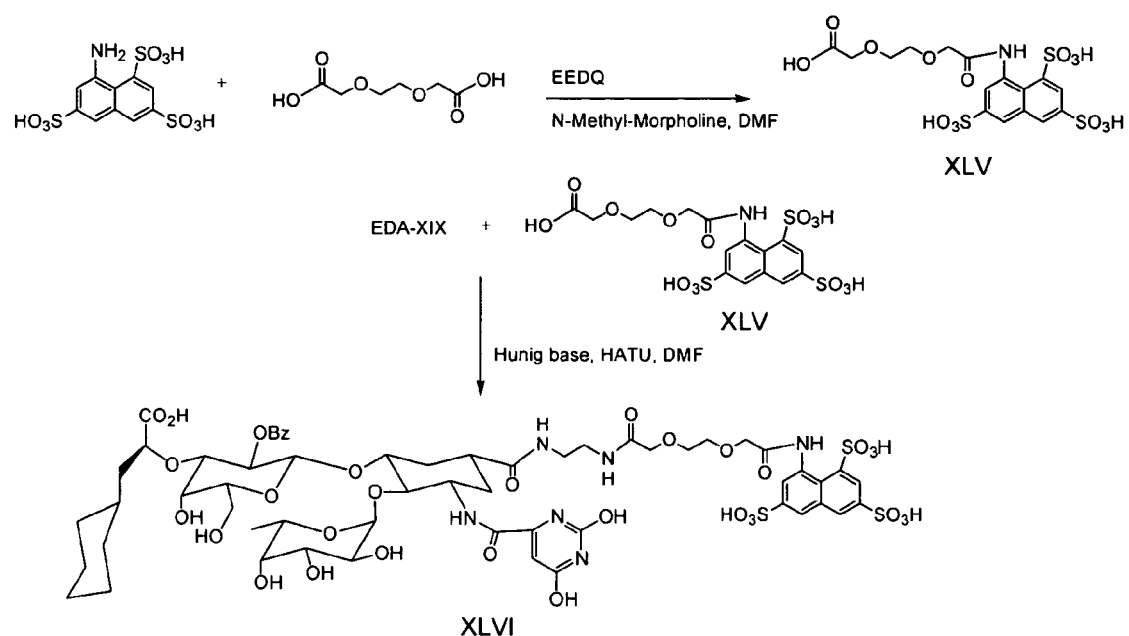
FIG. 14 is a diagram illustrating the synthesis of a glycomimetic-BASA.

Synthesis of Glycomimetic-BASA (FIG. 14)

Synthesis of compound XLV: To a solution of 3,6-dioxaoctanedioic acid (PEG, 200 mg, available commercially) in DMF (1 ml) is added Hunig base (0.4 ml) and then HATU (0.35 g) is added after 5 min. The solution is stirred at RT for 10 min and then solution of 8-aminonaphthalene-1,3,6-trisulfonic acid (50 mg, available commercially) in DMF is added. The reaction mixture is stirred for 4 h at RT and the solvent is evaporated off. The residue is purified by hplc (reverse-phase C18 column) to give XLV (25 mg).

Synthesis of compound XLVI: This synthesis is performed in the same way as described in example 10 using XLV and EDA-XIX from example 4 to give compound XLVI (4 mg).

Example 19

Figure 15:
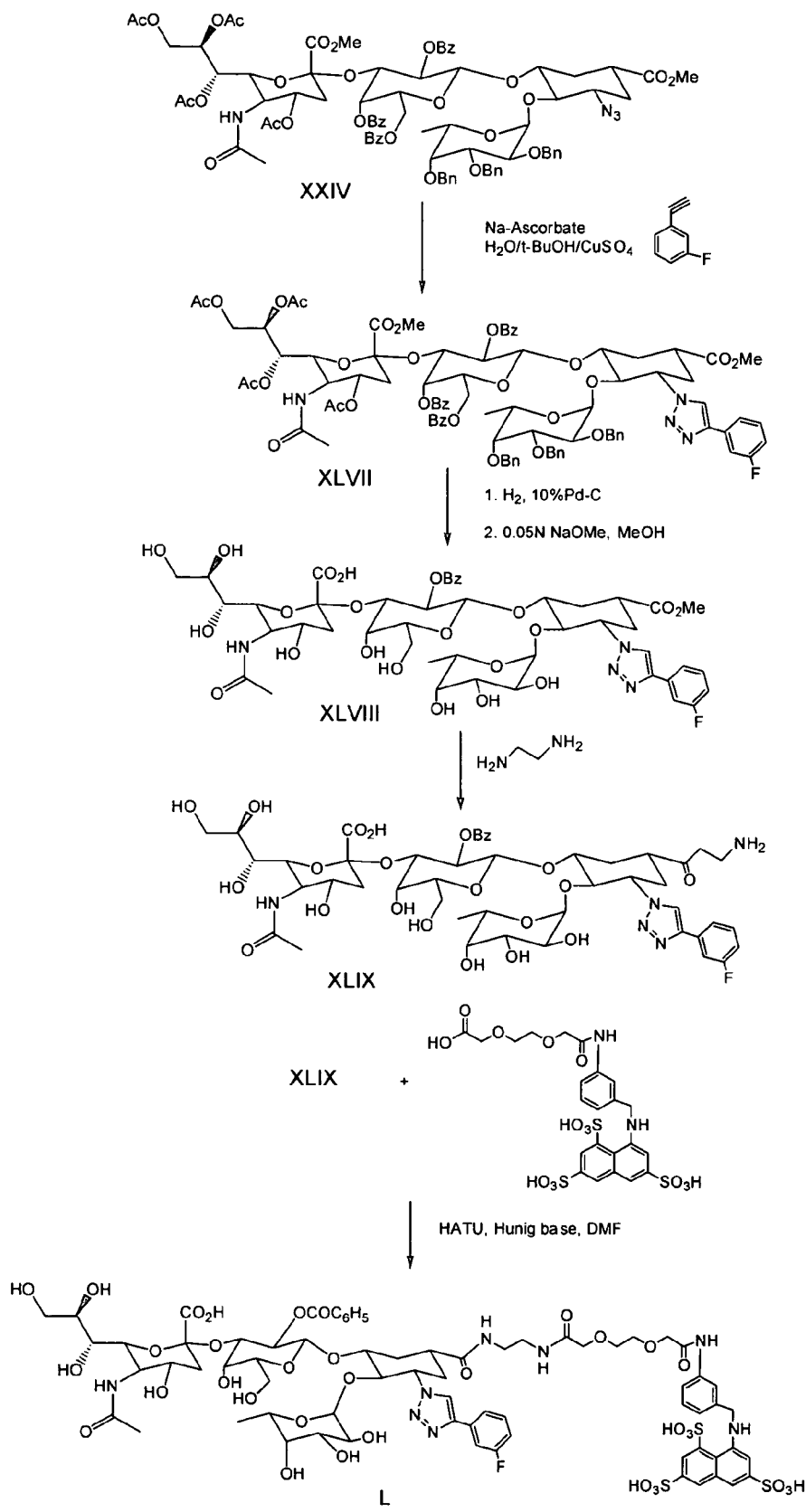
FIG. 15 is a diagram illustrating the synthesis of a glycomimetic-BASA.

Synthesis of Glycomimetic-BASA (FIG. 15)

Synthesis of XLVII: Starting with compound XXIV, this synthesis is performed in the same way as described for the synthesis of XLI to give compound XLVI.

Synthesis of XLVIII: Starting with compound XLVII, this synthesis is performed in the same way as described for compound XLIII (from XLI) to give compound XLVIII.

Synthesis of XLIX: Starting with compound XLVIII, this synthesis is performed in the same way as described for the synthesis of XLIV to give compound XLIX.

Synthesis of Glycomimetic-BASA (compound L): This synthesis is performed in the same way as described in example 10 using XXXIII from example 6 and XLIX to give compound L. Alternatively, XXXIII can be replaced with XLV from Example 18 for reaction with XLIX.

Example 20

Figure 16:
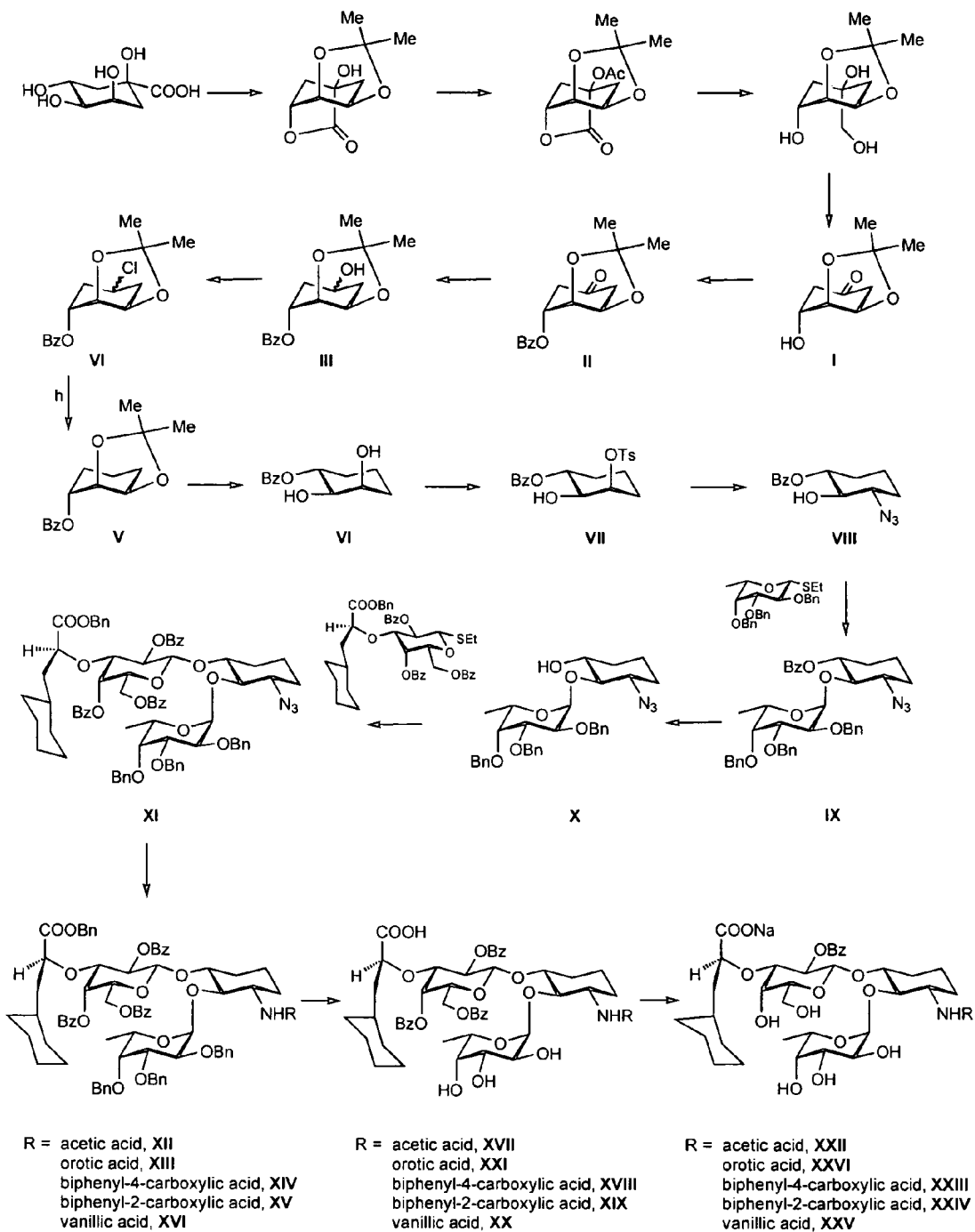
FIG. 16 is a diagram illustrating the synthesis of glycomimetics.

Synthesis of GlycomimeticS (FIG. 16)

Synthesis of Compound I: as described in the literature [*J. Org. Chem.* 54, 3738-3740 (1989); *Liebigs Annalen der Chemie* 575, 1 (1952)]

Synthesis of Intermediate II: I (2.8 g, 15.04 mmol), pyridine (4.8 ml, 60.15 mmol), benzoylchloride (3.5 ml, 30.07 mmol) and a catalytical amount of dimethyl aminopyridine are stirred in dichloromethane (6 ml) at room temperature ("r.t."). After 2 h, TLC control shows completion of the reaction. The reaction mixture then is diluted with ethyl acetate (200 ml) and washed with water, 1N aqueous HCl (ice-cooled), saturated aqueous NaHCO$_3$ and brine (each 50 ml). The aqueous layers are washed twice with ethyl acetate (2×150 ml), combined and dried with Na$_2$SO$_4$. After filtration and evaporation of the solvent the residue is purified by chromatography on silica gel (PE/EtOAc 4:1) to yield compound II (3.78 g, 86%).

Synthesis of Intermediate III: II (3.78 g, 13.02 mmol) and NaBH$_4$ are stirred in methanol (35 ml) at 0° C. After 30 min. the reaction mixture is quenched with water (15 ml) and neutralized with 1N aqueous AcOH. Again water (10 ml) is added and the mixture is extracted 3 times with dichloromethane (3×150 ml). The combined organic layers are dried with Na$_2$SO$_4$, filtered and evaporated. Chromatography of the residue on silica gel (PE/EtOAc 3.2) gives compound III (3.7 g, 97%). $[\alpha]_D$+79.78° (c=0.940, CH$_2$Cl$_2$);

Synthesis of Intermediate IV: To a solution of III (3.4 mg, 11.64 mmol) in CHCl$_3$ (50 ml, filtered on basic Alox) at r.t. under argon is added 1-chloro-N,N,2-trimethylpropenylamine (4.94 ml, 34.93 mmol) by a syringe. The reaction mixture is stirred at reflux until TLC control indicated completion of the reaction (30 min.) After cooling to r.t. the reaction mixture is quenched with triethylamine (6 ml) and evaporated (bath temperature 30° C.) to dryness. The residue is purified by chromatography on silica gel (PE/EtOAc 9:1) to yield compound IV (3.3 g, 92%).

Synthesis of Intermediate V: To a solution of IV (3.25 g, 10.47 mmol) in dry toluene (40 ml) under argon are added freshly distilled Bu$_3$SnH (30.58 ml, 115.14 mmol) and AlBN (1.7 g, 10.47 mmol). The reaction is refluxed. After 75 min., when TLC shows completion of the reaction, the reaction mixture is cooled to r.t. and then diluted with acetonitrile (50 ml). The solution is washed with hexane (50 ml) and the hexane layer is extracted again with acetonitrile (50 ml). The combined acetonitrile layers are evaporated. Chromatography of the residue on silica gel (toluene/EtOAc 14:1) yields compound V (2.66 g, 92%). $[\alpha]_D$-117.79° (c=1.810, CH$_2$Cl$_2$).

Synthesis of Intermediate VI: A solution of V (2.63 g, 9.54 mmol) in aqueous AcOH 80% is stirred at 80° C. When TLC control indicates completion of the reaction (30 min.), reaction mixture is cooled to r.t. After neutralizing with aqueous NaOH, the mixture is extracted 3 times with dichloromethane (3×200 ml). The combined organic layers are dried with Na$_2$SO$_4$, filtered and evaporated to dryness. The residue is purified by chromatography on silica gel (PE/EtOAc 3:2) to yield compound VI (2.01 g, 89%). $[\alpha]_D$-54.860° (c=1.420, CH$_2$Cl$_2$).

Synthesis of Intermediate VII: A solution of VI (1.98 g, 8.39 mmol), freshly recrystallized toluene-4-sulfonylchloride (1.9 g, 10.07 mmol), Bu$_2$SnO (2.09 g, 8.39 mmol) and triethylamine (1.8 ml, 16.78 mmol) in dry dichloromethane (40 ml) is stirred at r.t. under argon. After 20 h, TLC control indicated completion of the reaction. The reaction mixture is then quenched with methanol (15 ml) and then evaporated to dryness. Chromatography of the residue on silica gel (toluene/EtOAc 8:1) gives compound VII (2.65 g, 85%). $[\alpha]_D$-68.080° (c=0.448, CH$_2$Cl$_2$).

Synthesis of Intermediate VIII: A mixture of VII (640 mg, 1.71 mmol) and NaN$_3$ (555 mg, 8.55 mmol) in DMF (30 ml) is stirred under argon at 80° C. When TLC control shows completion of the reaction (after 1 h), the reaction mixture is cooled to r.t., diluted with dichloromethane (50 ml) and washed with water (50 ml). The aqueous layer is then extracted twice with dichloromethane (2×50 ml) and the combined organic layers are dried with Na$_2$SO$_4$, filtered and evaporated. The residue is purified by chromatography on silica gel (toluene/EtOAc 6:1) to yield compound VIII (391 mg, 87%). $[\alpha]_D$-69.39° (c=2.330, CH$_2$Cl$_2$).

Synthesis of Intermediate IX: To a stirred solution of ethyl 2,3,4-tri-O-benzyl-α-L-fucothiopyranoside (223 mg, 0.47 mmol) in dry dichloromethane (1 ml) at 0° C. under Ar atmosphere, bromine (48μ, 0.54 mmol) is added. After 5 min. the cooling bath is removed and the reaction mixture is stirred for additional 40 min. at r.t. To remove the excess of bromine, cyclohexene (50 μl) is added, leading to a decolorization of the reaction mixture. Then the reaction mixture is added to a pre-stirred solution (1 h, r.t.) of VIII (61 mg, 0.23 mmol), (Et)$_4$NBr (98 mg, 0.47 mmol) and powdered 4 Å molecular sieves (100 mg) in dichloromethane (1.6 ml) and DMF (1 ml). After 18 h, the reaction is quenched with pyridine (2 ml) and stirred for additional for 15 min., before it is diluted with EtOAc (50 ml) and washed with sat. aqueous KHCO$_3$, water and brine (each 50 ml). The aqueous layers are extracted twice with EtOAc (2×50 ml). The combined organic layers are dried with Na$_2$SO$_4$, filtered and evaporated to dryness. The residue is purified by chromatography on silica gel (toluene/EtOAc 9:1) to yield IX (116 mg, 73%). $[\alpha]_D$-95.96° (c=1.040, CH$_2$Cl$_2$).

Synthesis of Intermediate X: IX (530 mg, 0.78 mmol) in MeOH (10 ml) and a catalytical amount of freshly prepared NaOMe are stirred at r.t. under Ar for 48 h. The reaction mixture is neutralized with powdered Amberlyst-15 and filtered over Celite. The filtrate is evaporated to dryness and purified by chromatography on silica gel (toluene/EtOAc 9:1) to give compound X (380 mg, 85%). $[\alpha]_D$-76.425° (c=4.00, CH$_2$Cl$_2$).

Synthesis of Intermediate XI: A mixture of X (184 mg, 0.32 mmol), the galactose building block [375 mg, 0.4811 mmol, synthesis as described previously, *Helv. Chim. Acta* 83: 2893-2907 (2000)] and activated powdered molecular sieves 4 Å (200 mg) in dichloromethane (3 ml) is stirred at r.t. under argon for 4 h. Then DMTST [B] (165 mg, 0.64 mmol) is added in 4 equal portions over a period of 1.5 h to a pre-stirred mixture (4 h, r.t.) of activated powered molecular sieves 4 Å (100 mg) in dichloromethane (3 ml). After 92 h, when TLC control shows completion of the reaction, the reaction mixture is filtered over Celite and the filtrate is diluted with dichloromethane (50 ml). The organic layer is washed with sat. aqueous NaHCO$_3$ and brine (each 20 ml) and the aqueous layers are extracted twice with dichloromethane (2×50 ml). The combined organic layers are dried with Na$_2$SO$_4$, filtered and evaporated to dryness. The residue is purified by chromatography on silica gel (toluene/EtOAc 9:1) to yield compound XI (310 mg, 75%). $[\alpha]_D$-36.98° (c=2.32, CH$_2$Cl$_2$).

General Procedure A

Synthesis of Intermediate XII: To a stirred solution of XI (100 mg, 0.077 mol) in dry dichloromethane (3 ml), acetic acid chloride (27 μl, 0.387 mmol) is added. After 5 min. PPh$_3$ (101 mg, 0.387 mmol) is added and the solution is stirred at r.t. When TLC after 22 h shows completion of the reaction, the solvent is removed and the residue chromatographed on silica gel (toluene/EtOAc 2:1) yielding compound XII (43 mg, 43%). $[\alpha]_D$-55.33° (c=2.185, CH$_2$Cl$_2$).

Synthesis of Intermediate XIII: According to procedure A: XI (80 mg, 0.062 mol) with orotic acid chloride (59 mg, 0.310 mmol) and PPh$_3$ (81 mg, 0.310 mmol), 4 h, (dichloromethane/MeOH 25:1) gives compound XIII (35 mg, 40%). $[\alpha]_D$-26.08° (c=1.48, CH$_2$Cl$_2$).

Synthesis of Intermediate XIV: According to procedure A: XI (70 mg, 0.054 mmol) with biphenyl-4-carboxylic acid chloride (58 mg, 0.271 mmol) and PPh$_3$(71 mg, 0.271 mmol), 4 h, (toluene/EtOAc 6:1) gives XIV (22 mg, 28%). $[\alpha]_D$–32.11° (c=1.065, CH$_2$Cl$_2$).

Synthesis of Intermediate XV: According to procedure A: XI (45 mg, 0.035 mmol) with biphenyl-2-carboxylic acid chloride (125 mg. 0.577 mmol) and PPh$_3$ (151 mg, 0.577 mmol), 5 h, (toluene/EtOAc 6:1), gives compound XV (22 mg, 44%). $[\alpha]_D$–19.54° (c=1.10, CH$_2$Cl$_2$).

General Procedure B

Synthesis of Intermediate XVI: A mixture of XI (120 mg, 0.093 mmol) and PPh$_3$ (30 mg, 0.116 mmol) in CH$_2$Cl$_2$ (2 ml) and water (100 µl) is stirred for 44 h at r.t. Then the solvents are removed and the residue dissolved in CH$_2$Cl$_2$ (2 ml) and DIC (11.8 mg, 0.094 mmol) and the vanillic acid (24 mg, 0.139 mmol) are added. After the mixture is stirred at r.t. for additional 62 h, the solvents are removed and the crude product is purified by chromatography on silica gel (toluene/EtOAc 2.5:1) to give compound XVI (62 mg, 47%). $[\alpha]_D$–29.58° (c=2.86, CH$_2$Cl$_2$).

General Procedure C

Synthesis of Intermediate XVII: A mixture of XII (40 mg, 0.0306 mmol), Pd(OH)$_2$ (30 mg), dioxane (2 ml) and water (0.4 ml) is hydrogenated in a Parr-shaker under 5 bar at r.t. After 20 h TLC control indicated completion of the reaction. The reaction mixture is filtered over Celite and evaporated to dryness. Purification of the crude product by chromatography (CH$_2$Cl$_2$/MeOH 9:1) yielded XVII (20 mg, 69%). $[\alpha]_D$–43.50° (c=1.00, MeOH).

Synthesis of Intermediate XVIII: According to procedure C: XIV (26 mg, 0.018 mmol), Pd(OH)$_2$ (11 mg), dioxane (1.2 ml), water (0.25 ml), 50 h, (CH$_2$Cl$_2$/MeOH 2:1) gives XVIII (10 mg, 50%).

Synthesis of Intermediate XIX: According to procedure C: XV (22 mg, 0.015 mmol), Pd(OH)$_2$ (20 mg), dioxane (1 ml), water (0.25 ml), 22 h, (CH$_2$Cl$_2$/MeOH 15:1) gives compound XIX (13 mg, 82%). $[\alpha]_D$–9.50° (c=1.21, MeOH).

Synthesis of Intermediate XXI: According to procedure C: XIII (21 mg, 0.015 mmol), Pd(OH)$_2$ (20 mg), dioxane (1 ml), water (0.25 ml), 22 h, (CH$_2$Cl$_2$/MeOH 15:1) gives compound XXI (13 mg, 86%).

Synthesis of Intermediate XX: A mixture of XVI (20 mg, 0.0141 mmol), 10% Pd/C (20 mg) MeOH (2 ml) and AcOH (50 µl) is stirred under a hydrogen atmosphere. When TLC control indicated completion of the reaction (after 22 h), the mixture is filtered over celite and evaporated to dryness. Chromatography of the residue on silica gel (CH$_2$Cl$_2$/MeOH 2:1) gives XX (15 mg, quant.). $[\alpha]_D$–29.32° (c=1.105, MeOH).

General Procedure D

Synthesis of Product XXII: A solution of XVII (27 mg, 0.0278 mmol) in dry MeOH (1 ml) and a catalytic amount of freshly prepared NaOMe is stirred at r.t. under argon. After 1 h, TLC control shows completion of the reaction. The reaction mixture is neutralized with powdered amberlyst-15, filtered over Celite and the filtrate evaporated to dryness. The residue is dissolved in MeOH (20 ml) and filtered over ion-exchange Dowex Na⊕. The filtrate is evaporated to dryness and chromatography (CH$_2$Cl$_2$/MeOH/water 10:4:0.8) of the crude product gives XXII (12 mg, 56%). $[\alpha]_D$–97.49° (c=0.546, MeOH).

Synthesis of Product XXIII: According to procedure D: XVIII (9.0 mg, 0.0083 mmol), 2 h, (CH$_2$Cl$_2$/MeOH/water 10:3:0.5) gives compound XXIII (7.5 mg, quant.). $[\alpha]_D$–79.50° (c=0.400, MeOH).

Synthesis of Product XXIV: According to procedure D: XIX (23 mg, 0.0212 mmol), MeOH (2 ml), 2.5 h, (CH$_2$Cl$_2$/MeOH/water 10:3:0.5) gives compound XXIV (7.0 mg, 39%). $[\alpha]_D$–54.54° (c=0.586, MeOH).

Synthesis of Product XXV: According to procedure D: XX (19 mg, 0.0180 mmol), MeOH (2 ml), 4 h, (CH$_2$Cl$_2$/MeOH/water 10:3:0.5) gives compound XXV (10.5 mg, 70%.) $[\alpha]_D$–69.96° (c=0.793, MeOH).

Synthesis of Product XXVI: According to procedure D: XXI (19 mg, 0.0180 mmol), MeOH (2 ml), 4 h, (CH$_2$Cl$_2$/MeOH/water 10:3:0.5) gives compound XXVI (10 mg, 65%.).

Example 21

Figure 17A:
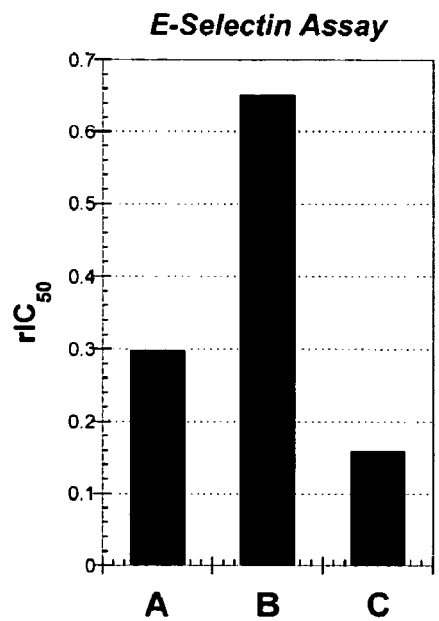
FIGS. 17A and 17B show a comparison of the activity of glycomimetic inhibitors in binding assays for E-selectins (FIG. 17A) and P-selectins (FIG. 17B) in vitro. A and B are glycomimetic-BASAs other than the present invention. C is the glycomimetic-BASA of FIG. 8C.

Assay for E-selectin Avtagonist Activity (FIG. 17A)

Wells of a microtiter plate (plate 1) are coated with E-selectin/hIg chimera (GlycoTech Corp., Rockville, Md.) by incubation for 2 hr at 37° C. After washing the plate 5 times with 50 mM TrisHCl, 150 mM NaCl, 2 mM CaCl$_2$, pH 7.4 (Tris-Ca), 100 µl of 1% BSA in Tris-Ca/Stabilcoat (SurModics, Eden Prairie, Minn.) (1:1, v/v) are added to each well to block non-specific binding. Test compounds are serially diluted in a second low-binding, round bottomed plate (plate 2) in Tris-Ca (60 µl/well). Preformed conjugates of SLea-PAA-biotin (GlycoTech Corp., Rockville, Md.) mixed with Streptavidin-HRP (Sigma, St. Louis, Mo.) are added to each well of plate 2 (60 µl/well of 1 µg/ml). Plate 1 is washed several times with Tris-Ca and 100 µl/well are transferred from plate 2 to plate 1. After incubation at room temperature for exactly 2 hours the plate is washed and 100 µl/well of TMB reagent (KPL labs, Gaithersburg, Md.) is added to each well. After incubation for 3 minutes at room temperature, the reaction is stopped by adding 100 µl/well of 1 M H$_3$PO$_4$ and the absorbance of light at 450 nm is determined by a microtiter plate reader.

Example 22

Figure 17B:
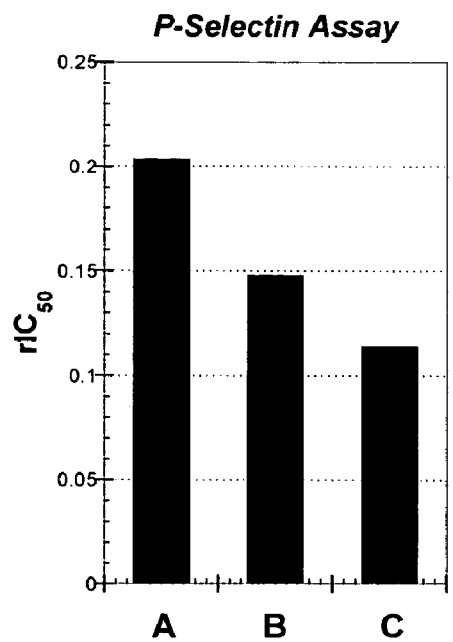
Figure 18:
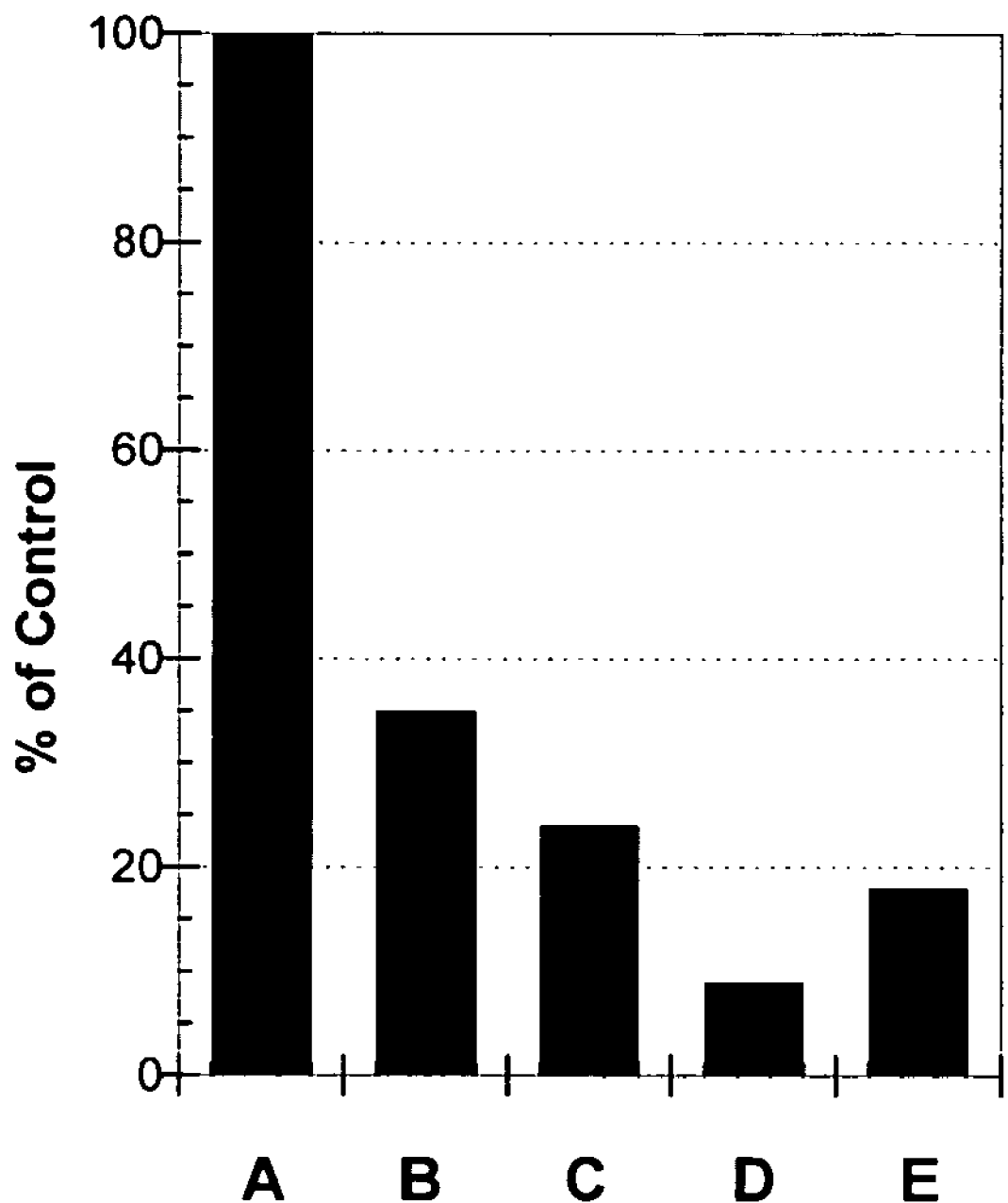
FIG. 18 shows the effect of glycomimetic-BASA of FIG. 8C on neutrophil migration. A is a vehicle only and E is a positive control (mixed antibodies). B, C and D are the glycomimetic-BASA of FIG. 8C at a dose of 5 mg/kg, 10 mg/kg, and 20 mg/kg, respectively.

Assay for P-selectin Antagonist Activity (FIG. 17B)

The neoglycoprotein, sialylLe$^a$-HSA (Isosep AB, Sweden) is coated onto wells of a microtiter plate (plate 1) and the wells are then blocked by the addition of 2% bovine serum albumin (BSA) diluted in Dulbecco's phosphate-buffered saline (DPBS). In a second microtiter plate (plate 2), test antagonists are serially diluted in 1% BSA in DPBS. After blocking, plate 1 is washed and the contents of plate 2 are transferred to plate 1. Pselectin/hIg recombinant chimeric protein (GlycoTech Corp., Rockville, Md.) is further added to each well in plate 1 and the binding process is allowed to incubate for 2 hours at room temperature. Plate 1 is then washed with DPBS and peroxidase-labelled goat anti-human Ig(γ) (KPL Labs, Gaithersburg, Md.) at 1 µg/ml is added to each well. After incubation at room temperature for 1 hour, the plate is washed with DBPS and then TMB substrate (KPL Labs) is added to each well. After 5 minutes, the reaction is stopped by the addition of 1 M H$_3$PO$_4$. Absorbance of light at 450 nm is then determined using a microtiter plate reader.

Example 23

Figure 19:
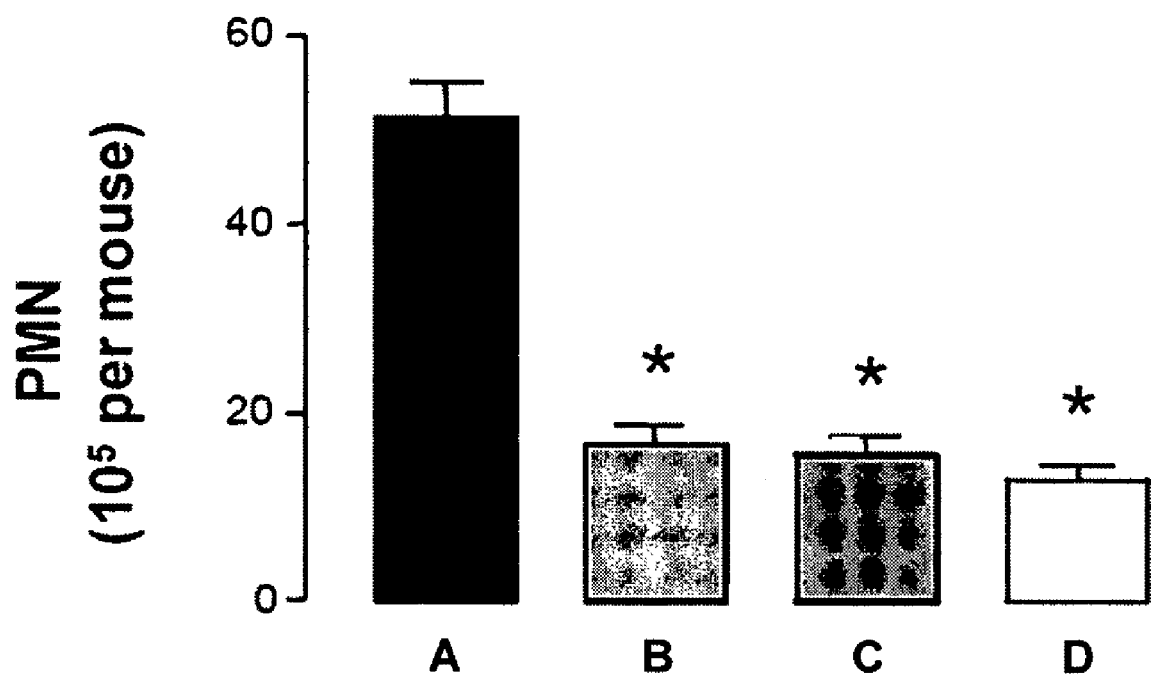
FIG. 19 shows a comparison of the effects of glycomimetic inhibitors on neutrophil migration in murine air pouch model. A is IL-1β+vehicle. B is IL-1β+the glycomimetic-BASA of FIG. 13. C is IL-1β+the glycomimetic-BASA of FIG. 8C. D is IL-1β+mixed antibodies (positive control). *P<0.05 vs. A (vehicle group).

Anti-inflammatory Mouse Model. Effects of Test Compound on IL-1β-Induced Neutrophil Migration to an Air Pouch in Vivo. (FIG. 19)

Animals

Male outbred Swiss albino mice (15-18 g body weight) are purchased from Bantin and Kingman (T.O. strain; Hull, Humberside) and maintained on a standard chow pellet diet with tap water ad libitum and a 12:00 h light/dark cycle. All animals are housed for 7 days prior to experimentation to allow body weight to reach ~25 g on the day of the experiment (day 6; see below)

Experimental Design

Air-pouches are formed on the back of mice by air injection (2.5 ml s.c.) on day 0 and day 3 (Perretti & Flower, 1993). A homogenous suspension of carboxymethylcellulose (CMC) is made at 0.5% w/v in PBS and murine recombinant IL-1β added to it at a concentration of 20 ng/ml.

Test Compound is given at time 0 just before IL-1β administration. An extra group is also added, in which a group of mice received CMC only (no IL-1β) to provide a basal negative control.

In all cases, air-pouches are washed 4 h after IL-1β with 2 ml of PBS containing 3 mM EDTA, and the number of migrated leukocytes (≧90% polymorphonuclear leukocytes, PMN) determined, by taking an aliquot (100 µl) of the lavage fluid and diluting 1:10 in Turk's solution (0.01% crystal violet in 3% acetic acid). The samples are then vortexed and 10 µl of the stained cell solution are placed in a Neubauer haematocymometer and neutrophils numbers counted using a light microscope (Olympus B061).

Compound Administration

On the day of the experiment, a fresh solutions of Test Compound is prepared in PBS Dulbecco's buffer supplemented with 1 mM $CaCl_2$ and $MgCl_2$. Monoclonal antibodies (mAb) against mouse P- or E-selectin are purchased from BD Pharmingen, whereas the anti-L-selectin mAb is from Serotec:

| | |
|---|---|
| Rat anti-mouse L selectin (clone MEL-14): | 1 mg |
| Rat anti-mouse P-selectin (clone RB40.34): | 0.5 mg/ml |
| Rat anti-mouse E-selectin (clone 10E9.6): | 0.5 mg/ml |

FIG. 19.

Mouse 6-day old air-pouches are inflamed with IL-1β (10 ng) at time 0; Example 17 glycomimetic-BASA (FIG. 13) and Example 12 glycomimetic-BASA (FIG. 8C) are given I.v. at time 0 and 4 h; and the mix of anti-selectin mAb is given I.v. at time 0.

Air-pouches are washed at the 8 h time-point and the number of migrated PMN determined by staining and light microscopy.

The n number is 9, 8, 7 and 8 mice per group A, B, C and D, respectively, in FIG. 19.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention is claimed:

1. A compound or salt thereof having the formula:

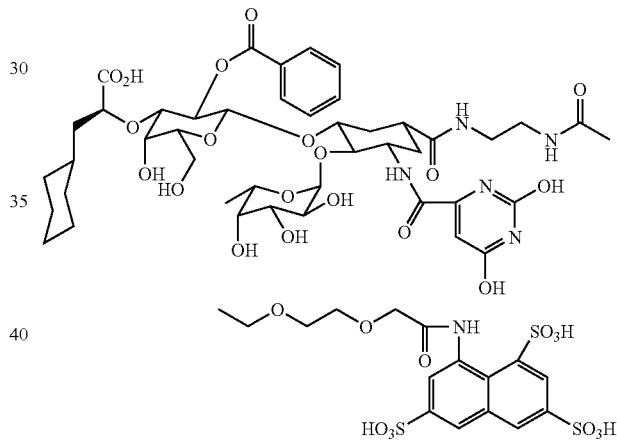

or physiologically acceptable salt thereof.

* * * * *

UNITED STATES PATENT AND TRADEMARK OFFICE
CERTIFICATE OF CORRECTION

PATENT NO. : 7,728,117 B2
APPLICATION NO. : 11/515343
DATED : June 1, 2010
INVENTOR(S) : John L. Magnani et al.

Page 1 of 1

It is certified that error appears in the above-identified patent and that said Letters Patent is hereby corrected as shown below:

Column 36, Line 26

"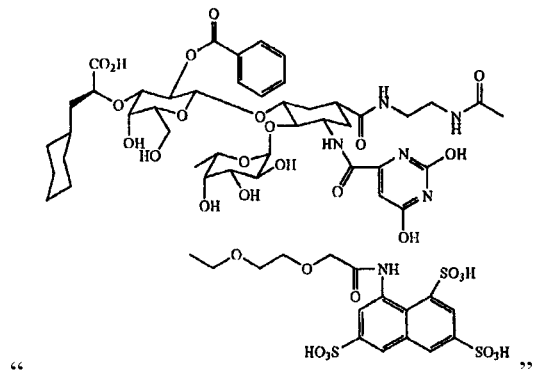"

should read as,

--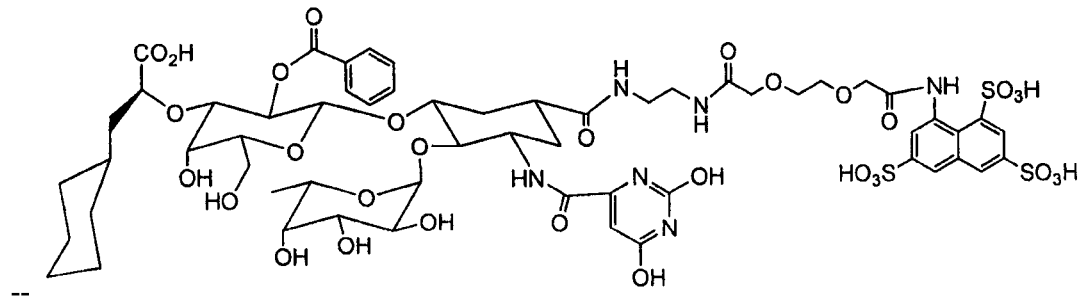--.

Signed and Sealed this
Fifth Day of April, 2011

David J. Kappos
*Director of the United States Patent and Trademark Office*